United States Patent
Gaharwar et al.

(10) Patent No.: US 10,034,958 B2
(45) Date of Patent: Jul. 31, 2018

(54) NANOCOMPOSITE HYDROGELS

(71) Applicants: The Brigham and Women's Hospital, Inc., Boston, MA (US); Massachusetts Institute of Technology, Cambridge, MA (US)

(72) Inventors: Akhilesh K. Gaharwar, Cambridge, MA (US); Reginald Keith Avery, Bel Air, MD (US); Gareth H. McKinley, Acton, MA (US); Alireza Khademhosseini, Cambridge, MA (US); Bradley David Olsen, Arlington, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/899,727

(22) PCT Filed: Jun. 19, 2014

(86) PCT No.: PCT/US2014/043251
§ 371 (c)(1),
(2) Date: Dec. 18, 2015

(87) PCT Pub. No.: WO2014/205261
PCT Pub. Date: Dec. 24, 2014

(65) Prior Publication Data
US 2016/0144068 A1    May 26, 2016

Related U.S. Application Data

(60) Provisional application No. 61/836,761, filed on Jun. 19, 2013.

(51) Int. Cl.
*A61L 26/00* (2006.01)
*A61K 9/00* (2006.01)
*A61K 9/51* (2006.01)
*A61L 15/32* (2006.01)

(52) U.S. Cl.
CPC ........ *A61L 26/0038* (2013.01); *A61K 9/0019* (2013.01); *A61K 9/5115* (2013.01); *A61L 15/32* (2013.01); *A61L 26/0004* (2013.01); *A61L 26/008* (2013.01); *A61L 26/0095* (2013.01); *A61L 2300/252* (2013.01); *A61L 2300/418* (2013.01); *A61L 2400/04* (2013.01); *A61L 2400/06* (2013.01); *A61L 2400/12* (2013.01)

(58) Field of Classification Search
CPC ... A61L 26/0038; A61L 26/008; A61L 26/009
See application file for complete search history.

(56) References Cited

U.S. PATENT DOCUMENTS

| | | | |
|---|---|---|---|
| 5,785,955 A | 7/1998 | Fischer | |
| 7,670,623 B2 | 3/2010 | Kotha et al. | |
| 8,106,030 B2 | 1/2012 | Hardy et al. | |
| 8,304,595 B2 | 11/2012 | Daniels et al. | |
| 8,703,208 B2 | 4/2014 | Liu et al. | |
| 2006/0018966 A1 | 1/2006 | Lin et al. | |
| 2007/0154510 A1 | 7/2007 | Wilcher et al. | |
| 2011/0171308 A1 | 7/2011 | Zhang et al. | |
| 2011/0275572 A1* | 11/2011 | Rafailovich | A61K 45/06 514/16.5 |

FOREIGN PATENT DOCUMENTS

| | | | |
|---|---|---|---|
| CA | 2635379 | | 4/2014 |
| CN | 102321255 A | * | 1/2012 |
| EP | 1983951 | | 10/2008 |
| EP | 2123309 | | 11/2009 |
| WO | WO 2007/074326 | | 7/2007 |
| WO | 2012/016695 | | 2/2012 |
| WO | 2012/040331 | | 3/2012 |
| WO | 2012/075087 | | 6/2012 |

OTHER PUBLICATIONS

Nichol et al. "Cell-laden microengineered gelatin methacrylated hydrogels", Biomaterials, Jul. 2010; 31 (21): 5536-5544.*
Cha, C. et al. "Microfluidics-assisted fabrication of geletatin-silica core-shell microgels for injectable tissue constructs", Biomacromolecules, 2014, 15(1), pp. 283-290 (Received Oct. 16, 2013). (Year: 2013).*
International Search Report and Written Opinion dated Oct. 16, 2014 in international application No. PCT/US14/43251, 12 pgs.
Assmann, et al., "Acceleration of autologous in vivo recellularization of decellularized aortic conduits by fibronectin surface coating," Biomaterials, Aug. 2013, 34(25):6015-6026.
Dawson and Oreffo, "Clay: New Opportunities for Tissue Regeneration and Biomaterial Design," Adv. Mater, 2013, 25 :4069-4086.
International Preliminary Report on Patentability dated Dec. 22, 2015 in international application No. PCT/US14/43251, 8 pgs.
Li et al., "Cytotoxicity and potency of mesocellular foam-26 in comparison to layered clays used as hemostatic agents," Toxicol. Res., 2013, 2:136-144.
Liu et al., "The improvement of hemostatic and wound healing property of chitosan by halloysite nanotubes," RSC Adv., 2014, 4:23540-23553.

* cited by examiner

*Primary Examiner* — Gina C Justice
(74) *Attorney, Agent, or Firm* — Fish & Richardson P.C.

(57) ABSTRACT

Provided herein are hemostatic compositions useful for treating wounds in a patient in need thereof. An exemplary hemostatic comprises gelatin or a derivative thereof and silicate nanoparticles. Methods of use, kits comprising the compositions, and a process of making the compositions are also provided.

23 Claims, 20 Drawing Sheets

4A

4B

4C

11A

11B

11C

NANOCOMPOSITE HYDROGELS

CROSS REFERENCE TO RELATED APPLICATIONS

This application is a national stage entry under 35 U.S.C. § 371 of PCT/US2014/043251, filed Jun. 19, 2014, and claims the benefit of U.S. Provisional Application Ser. No. 61/836,761, filed Jun. 19, 2013, the disclosures of which are incorporated herein by reference in their entirety.

TECHNICAL FIELD

This disclosure relates to hemostatic compositions, and more particularly to injectable and self-healing hemostats useful for clotting blood.

BACKGROUND

Wound healing refers to a complex series of biochemical and cellular events, which can include contracting, closing, and healing of a wound, which, in itself, can be a traumatic insult to the integrity of a tissue. Wound management contemplates protecting the wound from additional trauma and/or environmental factors that may delay the healing process. Towards this end, it advocates a combined systemic and local approach to facilitate wound healing, which can include the use of antibiotics and the application of a suitable dressing. One function of a wound dressing is to provide a healing environment by mimicking the natural barrier function of the epithelium. Accordingly, in practice, a wound dressing should, for example: i) control bleeding; ii) isolate and protect the wound or bleeding site from the external environment before healing can begin; iii) prevent further contamination or infection; and/or iv) maintain a moist micro-environment next to the wound surface.

SUMMARY

The present application provides, inter alia, a pharmaceutical composition, comprising gelatin or a derivative thereof, and silicate nanoparticles.

In some embodiments, the composition comprises about 0.5 percent to about 85 percent by weight of gelatin or a derivative thereof, and silicate nanoparticles together.

In some embodiments, the composition comprises about 0.5 percent to about 60 percent by weight of gelatin or a derivative thereof, and silicate nanoparticles together.

In some embodiments, the composition comprises about 0.5 percent to about 25 percent by weight of gelatin or a derivative thereof, and silicate nanoparticles together.

In some embodiments, the composition comprises about 0.5 percent to about 11 percent by weight of gelatin or a derivative thereof, and silicate nanoparticles together.

In some embodiments, the composition comprises about 3 percent to about 11 percent by weight of gelatin or a derivative thereof, and silicate nanoparticles together.

In some embodiments, the composition comprises about 0.5 percent to about 30 percent by weight of the silicate nanoparticles.

In some embodiments, the composition comprises about 0.5 percent to about 20 percent by weight of the silicate nanoparticles.

In some embodiments, the composition comprises about 0.5 percent to about 10 percent by weight of the silicate nanoparticles.

In some embodiments, the composition comprises about 2.25 percent to about 6.75 percent by weight of the silicate nanoparticles.

In some embodiments, the composition comprises about 1.5 percent to about 4.5 percent by weight of the silicate nanoparticles.

In some embodiments, the composition comprises about 0.75 percent to about 2.25 percent by weight of the silicate nanoparticles.

In some embodiments, the composition comprises about 0.5 percent to about 70 percent by weight of the gelatin or a derivative thereof.

In some embodiments, the composition comprises about 0.5 percent to about 60 percent by weight of the gelatin or a derivative thereof.

In some embodiments, the composition comprises about 0.5 percent to about 40 percent by weight of the gelatin or a derivative thereof.

In some embodiments, the composition comprises about 0.5 percent to about 20 percent by weight of the gelatin or a derivative thereof.

In some embodiments, the composition comprises about 0.5 percent to about 10 percent by weight of the gelatin or a derivative thereof.

In some embodiments, the composition comprises about 2.25 percent to about 6.75 percent by weight of the gelatin or a derivative thereof.

In some embodiments, the composition comprises about 1.5 percent to about 4.5 percent by weight of the gelatin or a derivative thereof.

In some embodiments, the composition comprises about 0.75 percent to about 2.25 percent by weight of the gelatin or a derivative thereof.

In some embodiments, the ratio of silicate nanoparticles to gelatin or a derivative thereof, is from about 0.1 to about 1.0.

In some embodiments, the composition further comprises water.

In some embodiments, the composition comprises about 0.5 percent to about 99 percent by weight of the water.

In some embodiments, the composition comprises about 30 percent to about 99 percent by weight of the water.

In some embodiments, the composition comprises about 50 percent to about 99 percent by weight of the water.

In some embodiments, the composition comprises about 70 percent to about 99 percent by weight of the water.

In some embodiments, the composition comprises about 90 percent to about 99 percent by weight of the water.

In some embodiments, the composition comprises about 80 percent to about 99 percent by weight of the water.

In some embodiments, the composition comprises about 90 percent to about 99 percent by weight of the water.

In some embodiments, the composition comprises about 91 percent to about 97 percent by weight of the water.

In some embodiments, the composition is a hydrogel.

In some embodiments, the composition comprises a gelatin derivative.

In some embodiments, the gelatin derivative is methacrylated gelatin (GelMA), acrylated gelatin, or thiolated gelatin.

In some embodiments, the gelatin derivative is methacrylated gelatin (GelMA).

In some embodiments, the silicate nanoparticles comprise silicate nanoplatelets.

In some embodiments, the silicate nanoplatelets comprise a positively charged edge and a negatively charged surface.

In some embodiments, the overall charge of the silicate nanoparticles is negative.

In some embodiments, the silicate nanoparticles are from about 5 nm to about 60 nm in diameter.

In some embodiments, the silicate nanoparticles are from about 10 nm to about 40 nm in diameter.

In some embodiments, the silicate nanoparticles are about 20 to 30 nm in diameter.

In some embodiments, the silicate nanoparticles are from about 0.5 nm to about 2 nm in thickness.

In some embodiments, the silicate nanoparticles are about 1 nm in thickness.

In some embodiments, the yield stress of the composition is from about 1 Pa to about 200 Pa.

In some embodiments, the yield stress of the composition is from about 1 Pa to about 100 Pa.

In some embodiments, the yield stress of the composition is from about 2 Pa to about 50 Pa.

In some embodiments, the yield stress of the composition is from about 1 Pa to about 25 Pa.

In some embodiments, the yield stress of the composition is from about 1 Pa to about 10 Pa.

In some embodiments, the yield stress of the composition is from about 1 Pa to about 5 Pa.

In some embodiments, the composition flows upon application of a pressure greater than the yield stress.

The present application also provides a pharmaceutical composition comprising gelatin and silicate nanoparticles.

In some embodiments, the composition comprises about 0.5 percent to about 85 percent by weight of gelatin and silicate nanoparticles together.

In some embodiments, the composition comprises about 0.5 percent to about 60 percent by weight of gelatin and silicate nanoparticles together.

In some embodiments, the composition comprises about 0.5 percent to about 25 percent by weight of gelatin and silicate nanoparticles together.

In some embodiments, the composition comprises about 1 percent to about 11 percent by weight of gelatin and silicate nanoparticles together.

In some embodiments, the composition comprises about 3 percent to about 11 percent by weight of gelatin and silicate nanoparticles together.

In some embodiments, the composition comprises about 0.5 percent to about 30 percent by weight of the silicate nanoparticles.

In some embodiments, the composition comprises about 0.5 percent to about 20 percent by weight of the silicate nanoparticles.

In some embodiments, the composition comprises about 0.5 percent to about 10 percent by weight of the silicate nanoparticles.

In some embodiments, the composition comprises about 2.25 percent to about 6.75 percent by weight of the silicate nanoparticles.

In some embodiments, the composition comprises about 1.5 percent to about 4.5 percent by weight of the silicate nanoparticles.

In some embodiments, the composition comprises about 0.75 percent to about 2.25 percent by weight of the silicate nanoparticles.

In some embodiments, the composition comprises about 0.5 percent to about 70 percent by weight of the gelatin.

In some embodiments, the composition comprises about 0.5 percent to about 60 percent by weight of the gelatin.

In some embodiments, the composition comprises about 0.5 percent to about 40 percent by weight of the gelatin.

In some embodiments, the composition comprises about 0.5 percent to about 20 percent by weight of the gelatin.

In some embodiments, the composition comprises about 0.5 percent to about 10 percent by weight of the gelatin.

In some embodiments, the composition comprises about 2.25 percent to about 6.75 percent by weight of the gelatin.

In some embodiments, the composition comprises about 1.5 percent to about 4.5 percent by weight of the gelatin.

In some embodiments, the composition comprises about 0.75 percent to about 2.25 percent by weight of the gelatin.

In some embodiments, the ratio of silicate nanoparticles to gelatin is from about 0.1 to about 1.0.

In some embodiments, the composition comprises about 6.75 percent by weight gelatin and about 2.25 percent by weight silicate nanoparticles; or about 4.5 percent by weight gelatin and about 4.5 percent by weight silicate nanoparticles; or about 2.25 percent by weight gelatin and about 6.75 percent by weight silicate nanoparticles; or about 4.5 percent by weight gelatin and about 1.5 percent by weight silicate nanoparticles; or about 3 percent by weight gelatin and about 3 percent by weight silicate nanoparticles; or about 1.5 percent by weight gelatin and about 4.5 percent by weight silicate nanoparticles; or about 2.25 percent by weight gelatin and about 0.75 percent by weight silicate nanoparticles; or about 1.5 percent by weight gelatin and about 1.5 percent by weight silicate nanoparticles; or about 0.75 percent by weight gelatin and about 2.25 percent by weight silicate nanoparticles.

In some embodiments, the composition further comprises water.

In some embodiments, the composition comprises about 0.5 percent to about 99 percent by weight of the water.

In some embodiments, the composition comprises about 30 percent to about 99 percent by weight of the water.

In some embodiments, the composition comprises about 50 percent to about 99 percent by weight of the water.

In some embodiments, the composition comprises about 70 percent to about 99 percent by weight of the water.

In some embodiments, the composition comprises about 80 percent to about 99 percent by weight of the water.

In some embodiments, the composition comprises about 90 percent to about 99 percent by weight of the water.

In some embodiments, the composition comprises about 91 percent to about 97 percent by weight of the water.

In some embodiments, the composition comprises about 6.75 percent by weight gelatin, about 2.25 percent by weight silicate nanoparticles, and about 91 percent by weight water; or about 4.5 percent by weight gelatin, about 4.5 percent by weight silicate nanoparticles, and about 91 percent by weight water; or about 2.25 percent by weight gelatin, about 6.75 percent by weight silicate nanoparticles, and about 91 percent by weight water; or about 4.5 percent by weight gelatin, about 1.5 percent by weight silicate nanoparticles, and about 94 percent by weight water; or about 3 percent by weight gelatin, about 3 percent by weight silicate nanoparticles, and about 94 percent by weight water; or about 1.5 percent by weight gelatin, about 4.5 percent by weight silicate nanoparticles, and about 94 percent by weight water; or about 2.25 percent by weight gelatin, about 0.75 percent by weight silicate nanoparticles, and about 97 percent by weight water; or about 1.5 percent by weight gelatin, about 1.5 percent by weight silicate nanoparticles, and about 97 percent by weight water; or about 0.75 percent by weight gelatin, about 2.25 percent by weight silicate nanoparticles, and about 97 percent by weight water.

In some embodiments, the silicate nanoparticles comprise silicate nanoplatelets.

In some embodiments, the silicate nanoplatelets comprise a positively charged edge and a negatively charged surface.

In some embodiments, the overall charge of the silicate nanoparticles is negative.

In some embodiments, the silicate nanoparticles are from about 5 nm to about 60 nm in diameter.

In some embodiments, the silicate particles are from about 10 nm to about 40 nm in diameter.

In some embodiments, the silicate nanoparticles are about 20 to about 30 nm in diameter.

In some embodiments, the silicate nanoparticles are from about 0.5 nm to about 2 nm in thickness.

In some embodiments, the silicate nanoparticles are about 1 nm in thickness.

In some embodiments, the composition is a gel.

In some embodiments, the gel is a hydrogel.

In some embodiments, the yield stress of the composition is from about 1 Pa to about 200 Pa.

In some embodiments, the yield stress of the composition is from about 1 Pa to about 100 Pa.

In some embodiments, the yield stress of the composition is from about 2 Pa to about 89 Pa.

In some embodiments, the yield stress of the composition is from about 2 Pa to about 50 Pa.

In some embodiments, the yield stress of the composition is from about 1 Pa to about 25 Pa.

In some embodiments, the yield stress of the composition is from about 1 Pa to about 10 Pa.

In some embodiments, the yield stress of the composition is from about 1 Pa to about 5 Pa.

In some embodiments, the composition flows upon application of a pressure greater than the yield stress.

In some embodiments, the gelatin is derived from a mammalian source.

In some embodiments, the gelatin is type-A porcine gelatin.

The present application also provides use of a composition provided herein as a hemostatic agent.

In some embodiments, the use of a composition provided herein is for use as an injectable hemostatic agent.

In some embodiments, the use of the injectable hemostatic agent comprises applying a pressure greater than the yield stress to the composition.

In some embodiments, the use of a composition provided herein is for use as a topical hemostatic agent.

The present application also provides a kit, comprising a composition provided herein.

In some embodiments, the kit further comprises one or more sterile syringes.

In some embodiments, the composition is preloaded into the one or more sterile syringes.

In some embodiments, the kit further comprises one or more sterile bandages.

In some embodiments, a pharmaceutically acceptable amount of the composition is preloaded onto a surface of the one or more sterile bandages.

In some embodiments, the kit further comprises one or more sterile surgical staples or one or more sterile surgical sutures.

In some embodiments, a pharmaceutically acceptable amount of the composition is preloaded onto a surface of the one or more sterile surgical staples.

In some embodiments, a pharmaceutically acceptable amount of the composition is preloaded onto a surface of the one or more sterile surgical sutures.

In some embodiments, the kit further comprises one or more sterile surgical sponges.

In some embodiments, a pharmaceutically acceptable amount of the composition is preloaded onto the one or more sterile surgical sponges.

Also provided herein is a sterile syringe comprising a composition provided herein.

The present application also provides a sterile bandage comprising a composition provided herein.

The present application also provides a sterile surgical staple comprising a composition provided herein.

The present application also provides a sterile surgical suture comprising a composition provided herein.

The present application also provides a sterile surgical sponge comprising a composition provided herein.

The present application also provides a sterile applicator comprising a composition provided herein.

The present application also provides a coating, comprising a pharmaceutically acceptable amount of a composition provided herein.

In some embodiments, the coating is preloaded onto a surface of a sterile surgical bandage.

In some embodiments, the coating is preloaded onto a surface of a sterile surgical staple.

In some embodiments, the coating is preloaded onto a surface of a sterile surgical suture.

In some embodiments, the coating is preloaded onto a sterile surgical sponge.

In some embodiments, the coating is applied as an aqueous solution.

In some embodiments, the coating comprises a composition wherein the yield stress of the composition is from about 1 Pa to about 200 Pa.

In some embodiments, the coating comprises a composition wherein the yield stress of the composition is from about 1 Pa to about 100 Pa.

In some embodiments, the coating comprises a composition wherein the yield stress of the composition is from about 2 Pa to about 89 Pa.

In some embodiments, the coating comprises a composition wherein the yield stress of the composition is from about 1 Pa to about 50 Pa.

In some embodiments, the coating comprises a composition wherein the yield stress of the composition is from about 1 Pa to about 25 Pa.

In some embodiments, the coating comprises a composition wherein the yield stress of the composition is from about 1 Pa to about 10 Pa.

In some embodiments, the coating comprises a composition wherein the yield stress of the composition is from about 1 Pa to about 5 Pa.

In some embodiments, the coating comprises a composition wherein the composition flows upon application of a pressure greater than the yield stress.

The present application also provides methods of treating a wound, comprising administering to a patient in need thereof, a composition provided herein.

In some embodiments, the wound comprises a wound of the skin on the patient.

In some embodiments, the wound comprises a wound of an organ in the patient.

In some embodiments, the wound comprises a wound of a blood vessel in the patient.

In some embodiments, the wound of a blood vessel comprises a wound of an artery in the patient.

In some embodiments, the wound of a blood vessel comprises a wound of a vein in the patient.

In some embodiments, the composition is administered by injection or topical administration.

In some embodiments, the composition is administered by injection.

In some embodiments, prior to administration, the composition is preloaded into a sterile syringe, preloaded onto a surface of a sterile bandage, preloaded onto a surface of a sterile surgical staple, preloaded onto a surface of a sterile surgical suture, or preloaded onto a sterile surgical sponge.

In some embodiments, the composition is preloaded into a sterile syringe.

In some embodiments, treating a wound comprises reducing the blood clotting time compared to the blood clotting time of an untreated wound.

In some embodiments, the blood clotting time is reduced by about 25% to about 85% compared to the blood clotting time of an untreated wound.

In some embodiments, the blood clotting time is reduced by about 32% compared to the blood clotting time of an untreated wound.

In some embodiments, the blood clotting time is reduced by about 54% compared to the blood clotting time of an untreated wound.

In some embodiments, the blood clotting time is reduced by about 77% compared to the blood clotting time of an untreated wound.

In some embodiments, the composition is administered locally to the wound.

The present application also provides a process of preparing a composition, comprising:

(a) combining silicate nanoparticles and water to form a first mixture;

(b) adding gelatin or a derivative thereof to the first mixture to form said composition.

In some embodiments, the first mixture comprises about 1 percent to about 10 percent by weight silicate nanoparticles.

In some embodiments, the first mixture comprises about 3 percent by weight silicate nanoparticles.

In some embodiments, the first mixture comprises about 6 percent by weight silicate nanoparticles.

In some embodiments, the first mixture comprises about 9 percent by weight silicate nanoparticles.

In some embodiments, prior to step (b), the gelatin or a derivative thereof is combined with water to form a second mixture.

In some embodiments, the second mixture is prepared at a temperature from about 0° C. to about 100° C.

In some embodiments, the second mixture is prepared at a temperature from about 35° C. to about 45° C.

In some embodiments, the second mixture comprises about 15 percent to about 20 percent by weight gelatin or a derivative thereof.

In some embodiments, the second mixture comprises about 18 percent by weight gelatin or a derivative thereof.

In some embodiments, step (b) is performed at a temperature from about 0° C. to about 100° C.

In some embodiments, step (b) is performed at a temperature of about room temperature.

In some embodiments, step (b) comprises adding gelatin to water to form a second mixture.

In some embodiments, the gelatin is mammalian gelatin.

In some embodiments, the mammalian gelatin is type-A porcine gelatin.

In some embodiments, step (b) comprises adding a gelatin derivative to water to form a second mixture.

In some embodiments, the gelatin derivative is methacrylated gelatin (GelMA), acrylated gelatin, or thiolated gelatin.

In some embodiments, the gelatin derivative is methacrylated gelatin (GelMA).

In some embodiments, the silicate nanoparticles comprise silicate nanoplatelets.

In some embodiments, the silicate nanoplatelets comprise a positively charged edge and a negatively charged surface.

In some embodiments, the overall charge of the silicate nanoparticles is negative.

In some embodiments, the silicate nanoparticles are from about 5 nm to about 60 nm in diameter.

In some embodiments, the silicate nanoparticles are from about 10 nm to about 40 nm in diameter.

In some embodiments, the silicate nanoparticles are from about 20 to about 30 nm in diameter.

In some embodiments, the silicate nanoparticles are from about 0.5 nm to about 2 nm in thickness.

In some embodiments, the silicate nanoparticles are about 1 nm in thickness.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
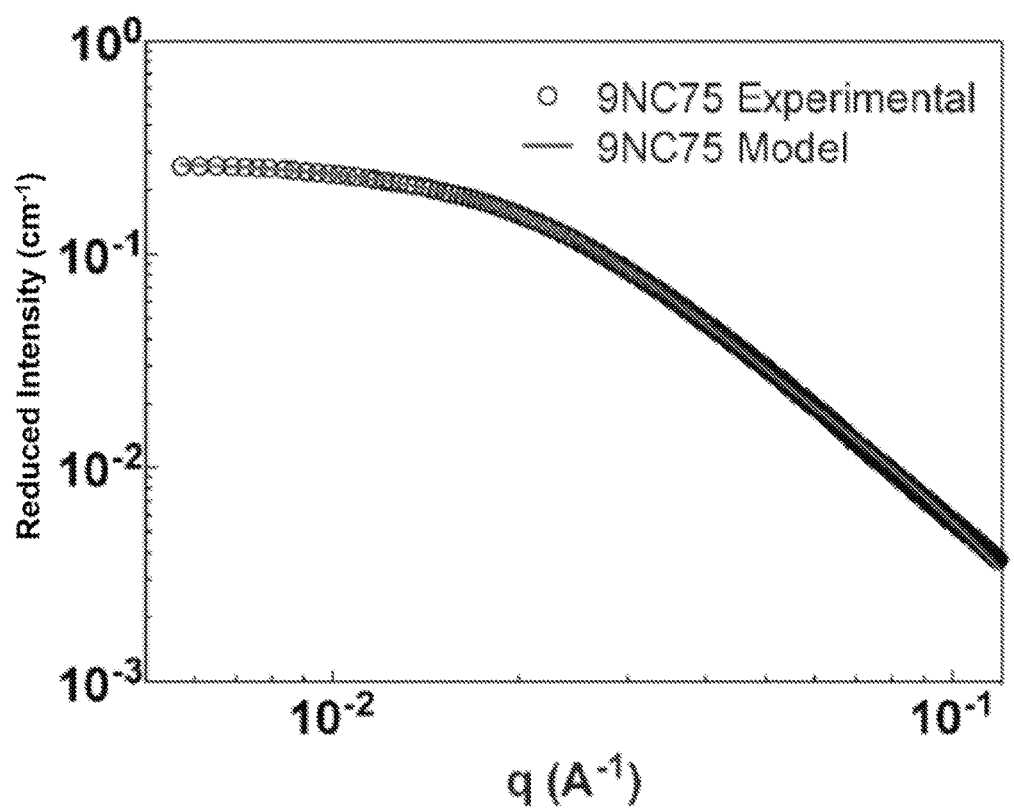
FIG. 1 shows a Small Angle X-ray Scattering (SAXS) intensity curve representative of composition 9NC75 overlapped with a thin disk model curve.

Wounds are generally classified as acute or chronic in accordance with their healing tendencies. Acute wounds, typically those received as a result of surgery or trauma, usually heal uneventfully within an expected time frame. Acute wounds include wounds such as active bleeding wound sites (e.g., wounds that have detectable, unclotted blood). The rapid control of topical bleeding at active bleeding wound sites can be important for wound management, for example, in the management of trauma (e.g., as a result of military exercises or surgery). As one example, hemorrhagic shock is a leading cause of death after penetrating injury on the battlefield. There is, therefore, a need for the development of new bioactive materials for the treatment of hemorrhagic shock that have the potential to increase the survivability of the injured soldier. While progress has been made in the development of combat hemostats over the last decade, the performance of existing materials is lacking, for example, for the treatment of intracavity wounds. In addition, many previously prepared hemostats have adverse side effects, and none of the current materials are biofunctional or bioresorbable.

Provided herein are hemostatic compositions for use with wounds, including traumatic injuries. In some embodiments, the biomaterials provided herein are injectable and can be introduced into a wound site, forming a physiologically stable artificial matrix and promoting the natural clotting cascade. For example, the compositions provided herein flow with minimal applied pressure during injection, providing a method of application that avoids additional patient trauma. Moreover, in some embodiments, the compositions provided herein, once in the wound, solidify to prevent biomaterial loss to unaffected areas.

Hemostatic Compositions

In one aspect, hemostatic compositions comprising gelatin or a derivative thereof, and silicate nanoparticles are provided.

As used herein, the term "gelatin", alone or in combination with other terms, refers to a mixture of proteins and peptides derived from the partial hydrolysis or denaturing of collagen. The intermolecular, intramolecular, and hydrogen bonds which stabilize collagen proteins and peptides are broken down to form gelatin, for example, by acid hydrolysis, alkali hydrolysis, or enzymatic hydrolysis. In some embodiments, the gelatin may be derived from a mammalian source. Examples of such gelatins include, but are not limited to porcine gelatin (e.g., type-A porcine gelatin, gelatin derived from porcine skin, gelatin derived from porcine bones, and the like), bovine gelatin (e.g., gelatin derived from bovine skin, type B bovine gelatin, gelatin derived from bovine bones, and the like), and equine gelatin.

In some embodiments, the hemostatic compositions disclosed herein comprise a gelatin derivative. As used here, the term "gelatin derivative", alone or in combination with other terms, refers to gelatin that has been reacted with various types of reagents to functionalize the gelatin (e.g., methacrylated gelatin (GelMA), acrylated gelatin, thiolated gelatin). For example, derivatives of gelatin may be prepared by reacting gelatin with an acid anhydride or acid chloride, including, but not limited to, phthalic anhydride, maleic anhydride, succinic anhydride, benzoic anhydride, isatoic anhydride, methacrylic anhydride, 3,4-dibromo phthalic anhydride, benzoyl chloride, p-nitro benzoyl chloride, 1-hydroxy-2-naphthoyl chloride, o-hydroxy benzoyl chloride, phthalyl chloride, and ethyl chlorocarbonate. In some embodiments, the hemostatic compositions disclosed herein comprise methacrylated gelatin (GelMA), acrylated gelatin, or thiolated gelatin.

In some embodiments, the hemostatic compositions disclosed herein comprise about 0.5 percent to about 70 percent by weight of gelatin or a derivative thereof, for example, from about 0.5 percent to about 60 percent by weight, about 0.5 percent to about 40 percent by weight, about 0.5 percent to about 20 percent by weight, about 0.5 percent to about 10 percent by weight, about 2.25 percent to about 6.75 percent by weight, about 1.5 percent to about 4.5 percent by weight, or from about 0.75 percent to about 2.25 percent by weight.

As used herein, the term "silicate nanoparticles", used alone or in combination with other terms, refers to silicate layered clays. Example silicate layered clays include, but are not limited to, laponite, montmorillonite, saponite, hectorite, kaolinite, palygorskite, and sepiolite. Silicate nanoparticles can be prepared, for example, by dialysis and similar purification techniques known in the art to remove any impurities. In some embodiments, overall charge of the silicate nanoparticles is negative. In some embodiments, the silicate nanoparticles are from about 5 nm to about 60 nm in diameter, for example, from about 10 nm to about 40 nm in diameter, from about 10 nm to about 30 nm in diameter, or from about 20 to about 30 nm in diameter. In some embodiments, the silicate nanoparticles are from about 0.5 nm to about 2 nm in thickness. In some embodiments, the silicate nanoparticles are about 1 nm in thickness.

In some embodiments, the silicate nanoparticles comprise silicate nanoplatelets. As used herein, the term "silicate nanoplatelets", used alone or in combination with other terms, refers to silicate layered clays characterized by a discotic charge distribution on the surface. Silicate nanoplatelets can be prepared, for example, by dispersion and sonication in an aqueous solution. In some embodiments, the silicate nanoplatelets comprise a positively charged edge and a negatively charged surface. In some embodiments, the overall charge of the silicate nanoplatelets is negative. In some embodiments, the silicate nanoplatelets are from about 5 nm to about 60 nm in diameter, for example, from about 10 nm to about 40 nm in diameter, from about 10 nm to about 30 nm in diameter, or from about 20 to about 30 nm in diameter. In some embodiments, the silicate nanoplatelets are from about 0.5 nm to about 2 nm in thickness. In some embodiments, the silicate nanoplatelets are about 1 nm in thickness In some embodiments, the hemostatic compositions provided herein comprise about 0.5 percent to about 30 percent by weight of the silicate nanoparticles, for example, about 0.5 percent to about 20 percent by weight, about 0.5 percent to about 10 percent by weight, about 2.25 percent to about 6.75 percent by weight, about 1.5 percent to about 4.5 percent by weight, or about 0.75 percent to about 2.25 percent by weight.

In some embodiments, the ratio of silicate nanoparticles to gelatin or a derivative thereof, is from about 0.1 to about 1.0, for example, about 0.1, about 0.2, about 0.3, about 0.4, about 0.5, about 0.6, about 0.7, about 0.8, about 0.9 or about 1.0. In some embodiments, the ratio of gelatin or a derivative thereof to silicate nanoparticles is from about 0.1 to about 1.0, for example, about 0.1, about 0.2, about 0.3, about 0.4, about 0.5, about 0.6, about 0.7, about 0.8, about 0.9 or about 1.0.

In some embodiments, the hemostatic compositions provided herein comprise about 0.5 percent to about 85 percent by weight of gelatin or a derivative thereof and silicate nanoparticles together, for example, from about 0.5 percent to about 70 percent by weight, from about 0.5 percent to about 60 percent by weight, from about 0.5 percent to about 50 percent by weight, from about 0.5 percent to about 40 percent by weight, from about 0.5 percent to about 30 percent by weight, about 0.5 percent to about 25 percent by weight, from about 0.5 percent to about 15 percent by weight, about 0.5 percent to about 11 percent by weight, or about 3 percent to about 11 percent by weight. In some embodiments, the hemostatic compositions provided herein comprise about 6.75 percent by weight gelatin and about 2.25 percent by weight silicate nanoparticles, about 4.5 percent by weight gelatin and about 4.5 percent by weight silicate nanoparticles, about 2.25 percent by weight gelatin and about 6.75 percent by weight silicate nanoparticles, about 4.5 percent by weight gelatin and about 1.5 percent by weight silicate nanoparticles, about 3 percent by weight gelatin and about 3 percent by weight silicate nanoparticles, about 1.5 percent by weight gelatin and about 4.5 percent by weight silicate nanoparticles, about 2.25 percent by weight gelatin and about 0.75 percent by weight silicate nanoparticles, about 1.5 percent by weight gelatin and about 1.5 percent by weight silicate nanoparticles, or about 0.75 percent by weight gelatin and about 2.25 percent by weight silicate nanoparticles.

In some embodiments, the hemostatic composition is a physically crosslinked gel comprising gelatin or a derivative thereof, and silicate nanoparticles. In some embodiments, the hemostatic composition is a physically crosslinked hydrogel comprising gelatin or a derivative thereof, and silicate nanoparticles.

Also provided are hemostatic compositions further comprising water, for example, ultra-pure water (e.g., Milli-Q) or buffered water (e.g., phosphate buffered saline). In some embodiments, the hemostatic compositions comprise from about 0.5 percent to about 99 percent by weight of water, for example, from about 30 percent to about 99 percent by weight, about 50 percent to about 99 percent by weight, about 70 percent to about 99 percent by weight, about 80 percent to about 99 percent by weight, about 90 percent to about 99 percent by weight, or about 91 percent to about 97 percent by weight.

In some embodiments, the hemostatic composition comprises, for example, about 6.75 percent by weight gelatin, about 2.25 percent by weight silicate nanoparticles, and about 91 percent by weight water, about 4.5 percent by weight gelatin, about 4.5 percent by weight silicate nanoparticles, and about 91 percent by weight water, about 2.25 percent by weight gelatin, about 6.75 percent by weight silicate nanoparticles, and about 91 percent by weight water, about 4.5 percent by weight gelatin, about 1.5 percent by weight silicate nanoparticles, and about 94 percent by weight water, about 3 percent by weight gelatin, about 3 percent by weight silicate nanoparticles, and about 94 percent by weight water, about 1.5 percent by weight gelatin, about 4.5 percent by weight silicate nanoparticles, and about 94 percent by weight water, about 2.25 percent by weight gelatin, about 0.75 percent by weight silicate nanoparticles, and about 97 percent by weight water, about 1.5 percent by weight gelatin, about 1.5 percent by weight silicate nanoparticles, and about 97 percent by weight water, or about 0.75 percent by weight gelatin, about 2.25 percent by weight silicate nanoparticles, and about 97 percent by weight water.

The compositions of provided herein can further include one or more additional pharmaceutical agents such as a steroid, anti-inflammatory compound, or immunosuppressant. Example steroids include corticosteroids such as cortisone, dexamethasone, hydrocortisone, methylprednisolone, prednisolone, and prednisone. Example anti-inflammatory compounds include aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib. Example immunosuppressants include azathioprine, chlorambucil, cyclophosphamide, cyclosporine, daclizumab, infliximab, methotrexate, and tacrolimus.

In some embodiments, the hemostatic composition is self-healing. As used herein, the expression "self-healing", used alone or in combination with other terms, refers to recovery of the elastic gel strength of a composition upon removal of a stress. In some aspects, a self-healing composition may recover elastic gel strength from about 2 seconds to about 1 minute after removal of a stress, for example, from 30 seconds to 1 min., from 30 seconds to 45 seconds, from 15 seconds to 1 minute, from 15 seconds to 45 seconds, from 15 seconds to 30 seconds, from 10 seconds to 15 seconds, from 10 seconds to 30 seconds, from 10 seconds to 45 seconds, from 10 seconds to 1 minute, from 5 seconds to 10 seconds, from 5 seconds to 25 seconds, from 5 seconds to 45 seconds, from 5 seconds to 1 minute, from 2 seconds to 10 seconds, from 2 seconds to 25 seconds, from 2 seconds to 45 seconds, or from about 2 seconds to 1 minute.

In some embodiments, the hemostatic compositions provided herein are shear thinning compositions. The expression "shear thinning" or "shear thinning behavior", refers to a decrease in viscosity (i.e. increasing flow rate) with an increasing rate of shear stress. For example, a shear thinning composition (i.e. a composition exhibiting shear thinning behavior) can exhibit a decrease in viscosity (i.e. increase in flow) upon application of an increasing rate of shear stress. As shown in Example 6, shear thinning behavior was not observed in the individual components of the compositions (e.g., gelatin, 9NC0), but was observed in compositions comprising gelatin and silicate nanoparticles (e.g., 9NC75).

In some embodiments, the hemostatic composition flows upon application of a pressure greater than the yield stress, for example, application of a pressure about 10% greater, about 20% greater, about 30% greater, about 40% greater, about 50% greater about 60% greater, about 70% greater, about 80% greater, about 90% greater, or about 100% greater than the yield stress. In some embodiments, the yield stress of the hemostatic composition is from about 1 Pa to about 200 Pa, for example, from about 1 Pa to about 100 Pa, from about 2 Pa to about 89 Pa, from about 2 Pa to about 50 Pa, from about 1 Pa to about 25 Pa, from about 1 Pa to about 10 Pa, or from about 1 Pa to about 5 Pa.

Hemostatic compositions are useful for accelerating blood clotting (e.g., reducing blood clotting time). Prior to the application of a hemostatic composition, an active bleeding wound site may be characterized as bleeding at a rate from about 0.5 mL/min to about 1000 mL/min, for example, 0.5 mL/min to 500 mL/min, 0.5 mL/min to 200 mL/min, 0.5 mL/min to 100 mL/min, 0.5 mL/min to 25 mL/min, 1 mL/min to 10 mL/min, 1 mL/min to 100 mL/min, 1 mL/min to 500 mL/min, 10 mL/min to 100 mL/min, 10 mL/min to 250 mL/min, 10 mL/min to 500 mL/min, 10 mL/min to 1000 mL/min, 50 mL/min to 250 mL/min, or 50 mL/min to 500 mL/min.

In neurological, ophthalmic, or spinal embodiments, where even the smallest amount of blood flow can have a negative effect on the patient, an active bleeding site may be characterized by a rate of blood flow from 0.1 mL/min to 20 mL/min, for example, 0.1 mL/min to 10 mL/min, 0.1 mL/min to 5 mL/min, 0.1 mL/min to 1 mL/min, 0.1 mL/min to 0.5 mL/min, 0.25 mL/min to 20 mL/min, 0.25 mL/min to 10 mL/min, 0.25 mL/min to 5 mL/min, 0.25 mL/min to 1 mL/min, or 0.25 mL/min to 0.5 mL/min.

In one aspect, a medical device useful in the treatment of a wound may comprise the hemostatic compositions provided herein. Example medical devices include, but are not limited to, a sterile syringe, a sterile bandage, a sterile surgical staple, a sterile surgical suture, a sterile surgical sponge, or a sterile applicator. In another aspect, the hemostatic compositions provided herein may be administered as a coating, for example, a coating on a surface of a sterile bandage, on the surface of a sterile surgical staple, on a surface of a sterile surgical suture, on a sterile surgical sponge, or on a surface of a sterile applicator.

In one aspect, the hemostatic compositions provided herein can be prepared by (a) combining silicate nanoparticles and water to form a first mixture and (b) adding gelatin or a derivative thereof to the first mixture to form the hemostatic composition. In some embodiments, step (b) comprises adding a gelatin derivative to the first mixture to form the hemostatic composition. In some embodiments, the gelatin derivative is methacrylated gelatin (GelMA), acrylated gelatin, or thiolated gelatin. In some embodiments, step (b) comprises adding gelatin to water to form a second mixture. In some embodiments, the gelatin is derived from a mammalian source. In some embodiments, the gelatin is type-A porcine gelatin. In some embodiments, the silicate nanoparticles are silicate nanoplatelets.

In some embodiments, the first mixture comprises about 1 percent to about 10 percent by weight silicate nanoparticles, for example, about 1 percent to about 9 percent, about 1 percent about 6 percent, or about 1 percent about 3 percent by weight silicate nanoparticles. In some embodiments, the first mixture comprises about 3 percent by weight silicate nanoparticles. In some embodiments, the first mixture comprises about 6 percent by weight silicate nanoparticles. In some embodiments, the first mixture comprises about 9 percent by weight silicate nanoparticles.

In some embodiments, prior to step (b), the gelatin or a derivative thereof is combined with water to form a second mixture. In some embodiments, the second mixture is prepared at a temperature from about 0° C. to about 100° C., for example, from about 0° C. to about 80° C., about 0° C. to about 60° C., about 0° C. to about 40° C., about 0° C. to about 20° C., about 10° C. to about 80° C., about 10° C. to about 60° C., or about 10° C. to about 40° C. In some embodiments, the second mixture is prepared at a temperature from about 35° C. to about 45° C.

In some embodiments, the second mixture comprises about 10 percent to about 50 percent by weight gelatin or a derivative thereof, for example, about 10 percent to about 40 percent, about 10 percent to about 30 percent, or about 10 percent to about 20 percent. In some embodiments, the second mixture comprises about 15 percent to about 20 percent by weight gelatin or a derivative thereof. In some embodiments, the second mixture comprises about 18 percent by weight gelatin or a derivative thereof.

In some embodiments, step (b) is performed at a temperature from about 0° C. to about 100° C., for example from about 0° C. to about 80° C., about 0° C. to about 60° C., about 0° C. to about 40° C., about 0° C. to about 20° C., about 10° C. to about 80° C., about 10° C. to about 60° C., or about 10° C. to about 40° C. In some embodiment, step (b) is performed at a temperature of about room temperature.

When employed as pharmaceuticals, the compositions provided herein can be administered in the form of pharmaceutical compositions. These compositions can be prepared in a manner well known in the pharmaceutical art, and can be administered by a variety of routes, depending upon whether local or systemic treatment is desired and upon the area to be treated.

Administration may be topical (including transdermal, epidermal, ophthalmic and to mucous membranes including intranasal, vaginal and rectal delivery), or parenteral. Parenteral administration includes intravenous, intraarterial, subcutaneous, intraperitoneal intramuscular, injection, or infusion; or intracranial, (e.g., intrathecal or intraventricular administration). Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, and powders. Conventional pharmaceutical carriers, aqueous, powder or oily bases, thickeners and the like may also be used in the compositions provided. In some embodiments, the hemostatic compositions provided herein are injectable. In some embodiments, the hemostatic compositions provided herein are topical.

In preparing the hemostatic compositions, the composition can be mixed with an excipient, diluted by an excipient or enclosed within such a carrier in the form of, for example, a bandage, a sponge, a syringe, or other container. When the excipient serves as a diluent, it can be a solid, semi-solid, or liquid material, which acts as a vehicle, carrier or medium for the composition. Some examples of suitable excipients include cellulose, water, buffered water, saline, and syrup.

The amount of the composition administered to a patient will vary depending upon the composition being administered, the purpose of the administration, the state of the patient, the manner of administration, and the like. In therapeutic applications, compositions can be administered to a patient to cure or at least partially arrest the symptoms and its complications. Effective doses will depend on the wound being treated as well as by the judgment of the attending clinician depending upon factors such as the severity of the wound, the age, weight and general condition of the patient, and the like.

The compositions provided herein can be effective over a wide dosage range and is generally administered in a therapeutically effective amount. It will be understood, however, that the amount of the composition actually administered will usually be determined by a physician, according to the relevant circumstances, including the condition to be treated, the chosen route of administration, the actual composition administered, the age, weight, and response of the individual patient, the severity of the patient's symptoms, and the like. An effective amount of a hemostatic composition may control bleeding, for example, to a rate of less than 0.03 mL/min, in a period of from about 10 seconds to about 20 minutes. In some embodiments, bleeding stops immediately, or in less than about 5 minutes, for example, from about 10 seconds to about 5 minutes, about 10 seconds to about 4 minutes, about 10 seconds to about 3 minutes, about 10 seconds to about 2 minutes, about 10 seconds to about 1 minute, about 10 seconds to about 45 seconds, or about 10 seconds to 30 seconds.

Methods

This disclosure also provides methods of treating a wound in a patient in need thereof. The method includes applying a hemostatic composition disclosed herein to the wound. In some embodiments, the wound comprises a wound of the skin on the patient. In some embodiments, the wound comprises a wound of an organ in the patient. In some embodiments, the wound comprises a wound of a blood vessel in the patient. In some embodiments, the wound of a blood vessel comprises a wound of an artery in the patient. In some embodiments, the wound of a blood vessel comprises a wound of a vein in the patient.

Application of the hemostatic composition typically includes contacting the hemostatic composition with the wound or bleeding site surface. The hemostatic composition is maintained in contact with the wound or bleeding site for a period of time sufficient to control the bleeding (e.g., to clot the blood, reduce the blood clotting time, or stop the bleeding). The application may include the use of pressure (e.g., by using an elastic bandage to maintain contact with the bleeding site). Alternatively, an internal wound may be packed with a hemostatic composition until hemostasis is achieved.

In some embodiments, a hemostatic composition is delivered to the wound site. For example, a catheter or needle may be used to deliver a hemostatic composition to an intravascular puncture site or to a biopsy site. In some embodiments, the catheter or the needle may be optionally coated with a hemostatic composition. In some embodiments, the composition is administered by injection or topical administration. In some embodiments, the composition is administered by injection. In some embodiments, the composition is administered locally to the wound. In some embodiments, prior to administration, the composition is preloaded into a sterile syringe, preloaded onto a surface of a sterile bandage, preloaded onto a surface of a sterile surgical staple, preloaded onto a surface of a sterile surgical suture, or preloaded onto a sterile surgical sponge. In some embodiments, the composition is preloaded into a sterile syringe.

When used for treating a wound, a hemostatic composition provided herein can control bleeding, for example, to a rate of less than 0.03 mL/min, in a period of from about 10 seconds to about 20 minutes. In some embodiments, bleeding stops immediately, or in less than about 5 minutes, for example, from about 10 seconds to about 5 minutes, about 10 seconds to about 4 minutes, about 10 seconds to about 3 minutes, about 10 seconds to about 2 minutes, about 10 seconds to about 1 minute, about 10 seconds to about 45 seconds, or about 10 seconds to 30 seconds. In some embodiments, treating a wound comprises reducing the blood clotting time compared to the blood clotting time of an untreated wound. In some embodiments, the blood clotting time is reduced by about 25% to about 85% compared to the blood clotting time of an untreated wound, for example, from about 25% to about 75%, about 25% to about 50%, about 25% to about 40%, or about 25% to about 30%. In some embodiments, the blood clotting time is reduced by about 32% compared to the blood clotting time of an untreated wound. In some embodiments, the blood clotting time is reduced by about 54% compared to the blood clotting time of an untreated wound. In some embodiments, the blood clotting time is reduced by about 77% compared to the blood clotting time of an untreated wound.

In some embodiments, the compositions provided herein can be used to inhibit or completely stop bleeding at the surface of the skin or of a parenchymal organ, such as the liver, kidney, spleen, pancreas, or lungs; or to control bleeding during surgery (e.g., abdominal, vascular, gynecological, dental, tissue transplantation surgery, amputation, etc.).

Kits

This disclosure also provides kits comprising a hemostatic composition as provided herein. The kit is useful, for example, in the treatment of a wound. Such kits can further include, if desired, one or more conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

In some embodiments, the kit comprises one or more sterile syringes. In some embodiments, the kit comprises the composition preloaded into one or more sterile syringes.

In some embodiments, the kit comprises one or more sterile bandages. In some embodiments, the kit comprises a pharmaceutically acceptable amount of the composition preloaded onto a surface of the one or more sterile bandages.

In some embodiments, the kit comprises one or more sterile surgical staples or one or more sterile surgical sutures. In some embodiments, the kit comprises a pharmaceutically acceptable amount of the composition preloaded onto a surface of the one or more sterile surgical staples.

In some embodiments, the kit comprises a pharmaceutically acceptable amount of the composition preloaded onto a surface of the one or more sterile surgical sutures. In some embodiments, the kit comprises one or more sterile surgical sponges. In some embodiments, the kit comprises a pharmaceutically acceptable amount of the composition preloaded onto the one or more sterile surgical sponges.

Definitions

As used herein, the term "hemostatic agent", alone or in combination with other terms, refers to a composition useful for accelerating the rate of blood clotting (i.e., reducing the blood clotting time) as compared to the average rate of biological blood coagulation in the absence of a hemostatic agent. For example, under typical conditions, human blood coagulates in about 5 to about 6 minutes.

As used herein, the term "gel", alone or in combination with other terms, is known in the art, and refers to a colloidal network or polymer network that is expanded throughout the whole volume by a fluid.

As used herein, the term "hydrogel", used alone or in combination with other terms, is known in the art, and refers to a colloidal network or polymer network that is expanded throughout the whole volume by water.

As used here, the expression "pharmaceutically acceptable" refers to compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the expressions "room temperature" or "rt", are understood in the art, and refer generally to a temperature (e.g. a reaction temperature) that is about the temperature of the room in which the reaction is carried out, for example, a temperature from about 20° C. to about 30° C.

As used herein, the term "wound", alone or in combination with other terms, refers to a tear, cut, or puncture of a localized area (e.g., skin, an organ, a blood vessel, and the like). The term "wound" may refer to an "open wound" or a "closed wound" (i.e., a contusion). Example "open wounds" include, but are not limited to, abrasions, amputations, avulsions, incisions, lacerations, punctures, penetrations, and the like. Example "closed wounds" include, but are not limited to, hematomas, crush injuries, intracavity wounds, internal wounds resulting from blunt trauma, incompressible bleeding, and the like.

As used herein, the term "active bleeding wound site", means, at a minimum, that unclotted blood is present in the wound (e.g., extravascular blood, particularly where the surface of a tissue has been broken, or an artery, vein, or capillary system has been compromised). The rate of blood flow from an active bleeding wound site can vary depending on the nature of the wound, for example, from about 0.5 mL/min to about 1000 mL/min. Some active bleeding wound sites may exhibit higher rates of blood flow (e.g., punctures of major arteries such as the aorta).

As used herein, the term "yield stress", used alone or in combination with other terms, refers to a magnitude of stress under which an elastic composition flows. In some aspects, yield stress may be characterized by about a 5% departure of the stress from the initial linearity on a stress-strain plot.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. Compositions of the Examples have been found to be shear thinning hemostatic compositions (i.e., compositions that promote hemostasis and exhibit shear thinning behavior), according to at least one assay described herein.

EXAMPLES

General Methods.

Physical mixtures of gelatin and silicate nanoplatelets were used to formulate the compositions disclosed herein. Synthetic silicate nanoplatelets (Laponite XLG) were purchased from Southern Clay Products, Inc. (Louisville, Ky.). Type-A porcine skin gelatin was obtained from Sigma Aldrich (Milwaukee, Wis.).

As a general procedure, silicate nanoplatelets were exfoliated in ultrapure (Milli-Q) water using a vortexer to enhance the surface area available for interaction with gelatin. Next, a gelatin stock, heated to liquefy the solution, was vigorously mixed with the exfoliated silicate at room temperature. Vigorous agitation was necessary to prevent clumping of the nanoplatelets during gelation; however, the nanoplatelets were stably dispersed after the gel had set.

The compositions of the examples were prepared with total solid concentrations (i.e., gelatin+silicate nanoplatelets) of 3, 6, and 9 weight percent and a gelatin:nanoplatelet ratio of from about 0:1 to about 1:0. Compositions of the examples are labeled as "xNCy", where "x" represents the total solid weight percent and "y" is percent of the total solid weight percent that is nanoplatelet. In the absence of silicate nanoplatelets, the gelatin solution was a viscous liquid at 37° C. Upon mixing silicate nanoplatelets with gelatin, the composition gelled in about 1 minute.

Oscillatory shear rheology was performed over a temperature range from 15° C. to 45° C., mimicking common environmental and physiological temperatures that the compositions may be exposed during sample preparation and in vivo applications.

Small Angle X-Ray Scattering (SAXS) was performed at the National Synchrotron Light Source (NSLS) at Brookhaven National Laboratory at beamline X27C. Samples were placed in a 1 mm thick washer and sealed between Kapton tape. Samples were equilibrated at 37° C. and 20° C. for 20 minutes prior to data collection. Scattering patterns were collected for 30 seconds per sample. Radial integration of the two dimensional scattering pattern was performed to yield a one dimensional scattering curve, which was corrected for empty cell and dark field scattering. Thin disk form factor model fitting was performed in MatLab using a nonlinear fit algorithm to fit the radius and a Gaussian distribution for polydispersity of the composition.

An Anton Paar MCR 301 rheometer was used for mechanical testing. A 25 mm diameter parallel plate geometry with a gap height of 500 μm was used for temperature sweeps and mineral oil was placed around the circumference of the plate to prevent evaporation of water from the composition for all tests. Compositions were equilibrated for 10 minutes prior to testing, followed by a 2 minute steady shear at $10\ s^{-1}$. 10 s of equilibrium time was sufficient for the viscosity to return to a higher plateau value, after which point testing was initiated. Frequency and shear rate sweeps were performed at 20 and 37° C., with frequencies from 0.001-100 Hz at 1% strain and shear rates from 0.001 to 100 $s^{-1}$ with 10 points/decade. Frequency sweeps were performed with a cone geometry (25 mm diameter, 1° angle, 50 μm truncation gap). Stress-controlled temperature sweeps were performed from 15-45° C. at 10 Pa stress and 1 Hz. All other tests were performed at 37° C. Oscillatory stress sweeps were performed from 0.01-100 Pa at 1 Hz. Strain Sweeps were performed from 0.01-1000% at 1 Hz. Recovery testing was conducted at 1 Hz by applying 100% strain, a value outside of the linear viscoelastic range, followed by 1% strain for 5 minutes to monitor gel recovery. Interfacial strength was also measured by applying a linearly increasing strain to a system of a composition and coagulated blood. Shear stress was measured until 1,800% strain. The maximum stress attained was used as a measure of the strength of the clot system.

Zeta potentials of gelatin and silicate nanoplatelets were determined in ultrapure water (Milli-Q) and phosphate buffered saline (PBS), pH 7.4 (Invitrogen) using a 633 nm laser in a Malvern ZEN3600 (Malvern Instruments, UK). Silicate nanoplatelets were dissolved with vigorous agitation (vortexing) while gelatin was dissolved with stirring at 40° C.

Example 1. Gelatin-Silicate Nanoparticle Composition Formulation

Stock solutions of 18% (w/w) gelatin and 9, 6, or 3% (w/w) silicate nanoplatelets were prepared in water. Milli-Q water was heated to 40° C. to dissolve gelatin and 4° C. water was used for nanoplatelet stock solutions to slow gelation and allow for full dissolution of nanoplatelet particles prior to gelling. The nanoplatelet gels were kept at room temperature to fully hydrate until a clear gel formed. The compositions were again heated and vortexed at 3000 rpm for 5 minutes to achieve the appropriate solid concentration and nanoplatelet loading. Once formed, the compositions were stored at 4° C.

Composition 9NC0 had a gel-sol transition temperature of 32° C., too low for application as a hemostat. However, the addition of silicate nanoplatelets to gelatin improved the thermal stability, increasing the sol-gel transition to above 45° C. for compositions having total solids concentrations of 6 weight percent or greater. In contrast, composition having a total solid concentration of 3 weight percent were not solid within the experimentally observed temperature range. Physiological stability was observed for all compositions having a total solids concentration of 9 weight percent. Physiological stability was also observed for compositions 6NC50, 6NC75, and 6NC100. Weight percentages of example compositions is shown below in Table 1.

TABLE 1

| Composition | Gelatin (wt %) | Nanoplatelets (wt %) | Water (wt %) |
| --- | --- | --- | --- |
| 9NC0 | 9 | 0 | 91 |
| 9NC25 | 6.75 | 2.25 | 91 |
| 9NC50 | 4.5 | 4.5 | 91 |
| 9NC75 | 2.25 | 6.75 | 91 |
| 9NC100 | 0 | 9 | 91 |
| 6NC0 | 6 | 0 | 94 |
| 6NC25 | 4.5 | 1.5 | 94 |
| 6NC50 | 3 | 3 | 94 |
| 6NC75 | 1.5 | 4.5 | 94 |
| 6NC100 | 0 | 6 | 94 |
| 3NC0 | 3 | 0 | 97 |
| 3NC25 | 2.25 | 0.75 | 97 |
| 3NC50 | 1.5 | 1.5 | 97 |
| 3NC75 | 0.75 | 2.25 | 97 |
| 3NC100 | 0 | 3 | 97 |

Example 2. Composition Degradation

Composition samples were placed in 2.0 mL Eppendorf tubes and weighed. Each sample was centrifuged in a swinging bucket rotor centrifuge to obtain a flat interface. Each sample was then soaked in phosphate buffered saline (PBS, pH 7.4; Invitrogen), stored at 37° C. At set times, the PBS was removed, and the composition was reweighed. The change in weight was recorded up to 24 hours after initial soaking. PBS was replaced after each weighing.

Example 3. Small Angle X-Ray Scattering

Figure 2:
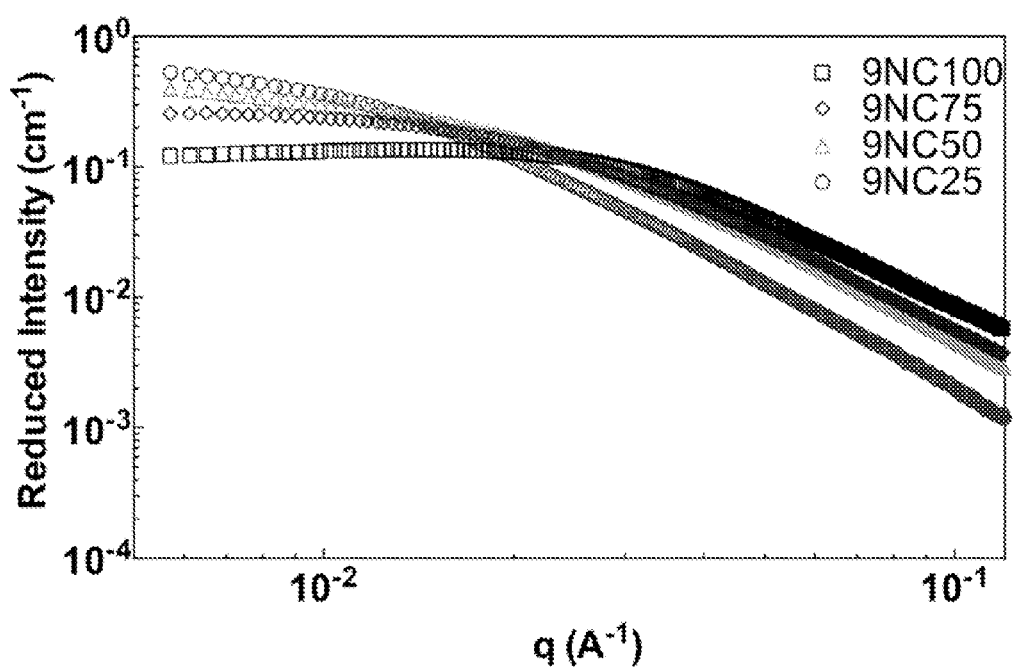
FIG. 2 shows Small angle X-ray scattering (SAXS) intensity curves representative of compositions 9NC100, 9NC75, 9NC50, and 9NC25.

Scattering measurements of gelatin-silicate nanoparticle compositions suggested the presence of disk shaped particles, indicating that clay particles remain exfoliated in the composition. Small Angle X-ray Scattering (SAXS) intensity curves of the compositions exhibited a power law decay with an exponent of −2 at high q, the scattering vector, characteristic of disk-shaped scatterers. The scattering intensity from 9NC75 can be fit with a thin disk model with a radius of 9.5±2.7 nm, in agreement with the reported size of the silicate nanoplatelets, as shown in FIG. 1. The SAXS intensity curves suggest that scattering was produced from individual nanoplatelets dispersed within the gelatin and not aggregates of nanoplatelets. The SAXS intensity curves for compositions 9NC100, 9NC75, 9NC50, and 9NC25 are shown in FIG. 2.

Figure 3:
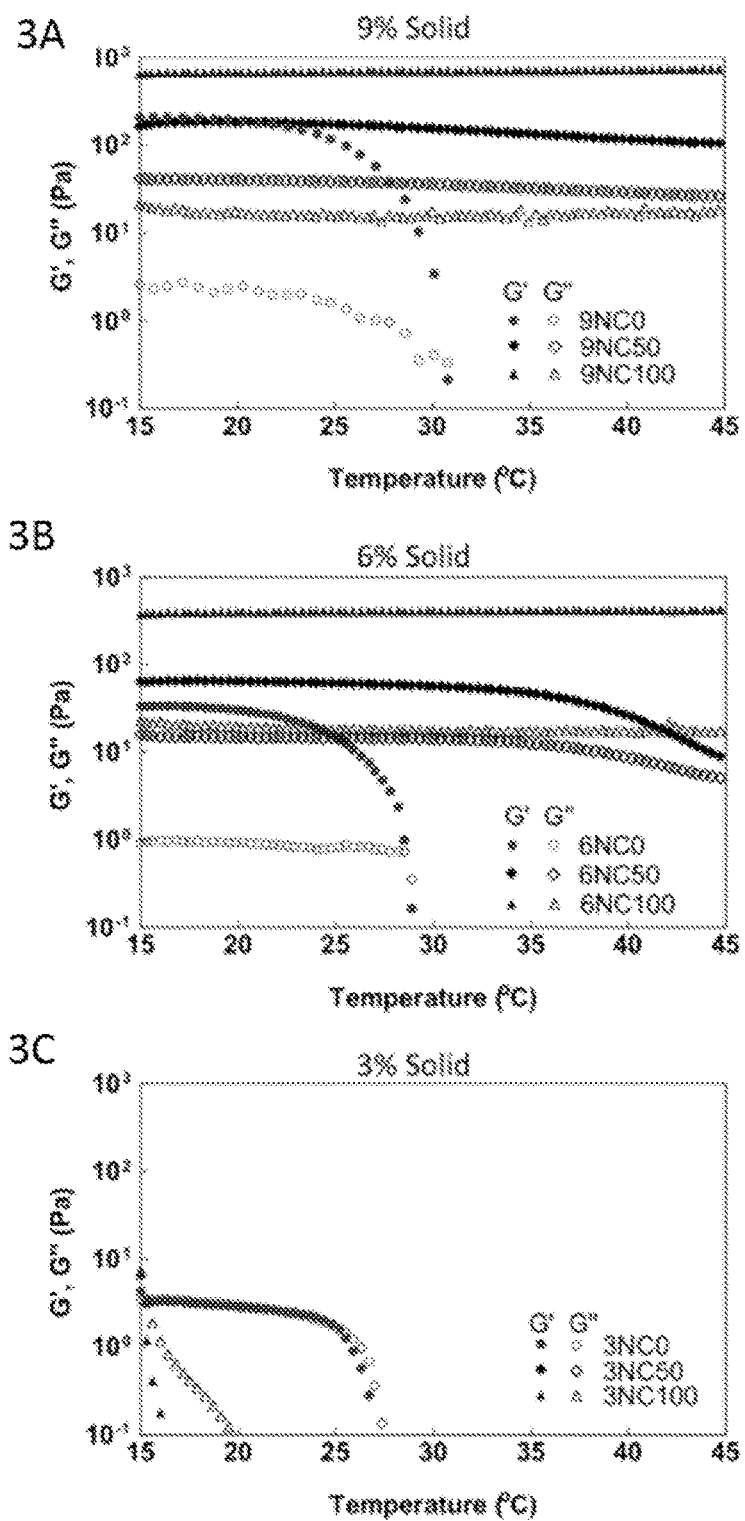
FIG. 3A shows the storage modulus (G') and loss modulus (G") of gelatin and compositions comprising 9 total weight percent solids in a PBS solution from 15° C. to 45° C. at 10 Pa stress and 1 Hz.
FIG. 3B shows the storage modulus (G') and loss modulus (G") of gelatin and compositions comprising 6 total weight percent solids in a PBS solution from 15° C. to 45° C. at 10 Pa stress and 1 Hz.
FIG. 3C shows the storage modulus (G') and loss modulus (G") of gelatin and compositions comprising 3 total weight percent solids in a PBS solution from 15° C. to 45° C. at 10 Pa stress and 1 Hz.

Example 4. Effect of Silicate Nanoplatelets on Physiological Stability of Compositions Storage modulus (G') and loss modulus (G") of gelatin and gelatin-silicate compositions with total solid concentrations of 9, 6, and 3 weight percent were monitored from 15° C. to 45° C. Gelatin (NC0) was observed to flow at all solid concentrations above 32° C. The addition of silicates improved the thermal stability of the composition network. All temperature sweeps were performed at 10 Pa stress and 1 Hz and are shown in FIG. 3.

Figure 4:
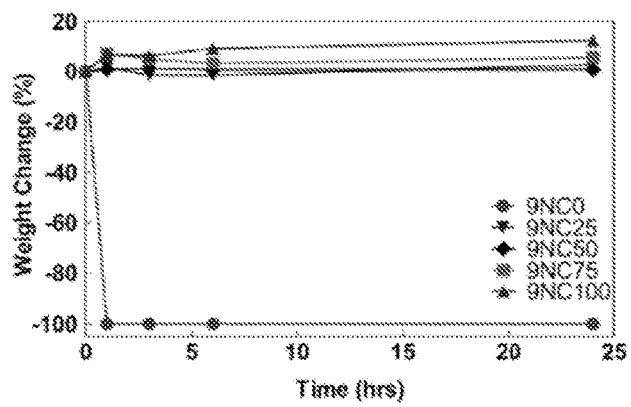
FIG. 4A shows the weight change percentage over time of compositions comprising 9 total weight percent solids in a PBS solution at 37° C.
FIG. 4B shows the weight change percentage over time of compositions comprising 6 total weight percent solids in a PBS solution at 37° C.
FIG. 4C shows the weight change percentage over time of compositions comprising 3 total weight percent solids in a PBS solution at 37° C.
Figure 4:
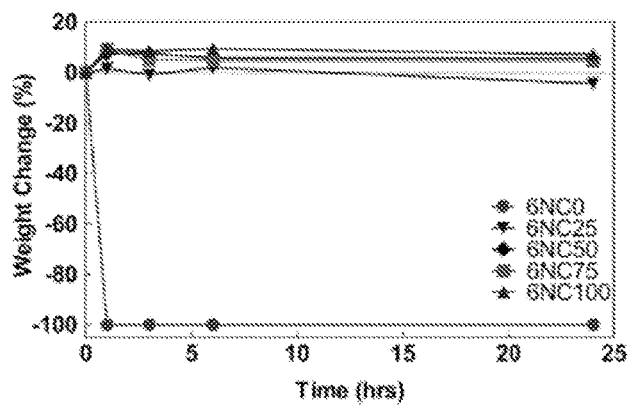
Figure 4:
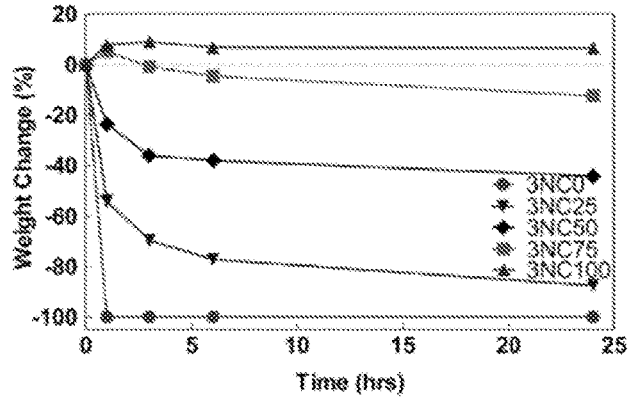

Example 5. Effect of Silicate Nanoplatelets on the Stability of Hydrogel Compositions in Physiological Solution Physiological stability was determined by measuring the weight of compositions with total solid concentration of 9, 6, and 3 weight percent stored in phosphate buffered solution (PBS) at 37° C. Gelatin (NC0) immediately dissolved in PBS, while compositions having a total solid concentration of 6 and 9 weight percent maintained their structural integrity throughout a 24 hour test, as shown in FIG. 4.

Example 6. Linear Viscoelastic Range of Hydrogel Compositions

Figure 5:
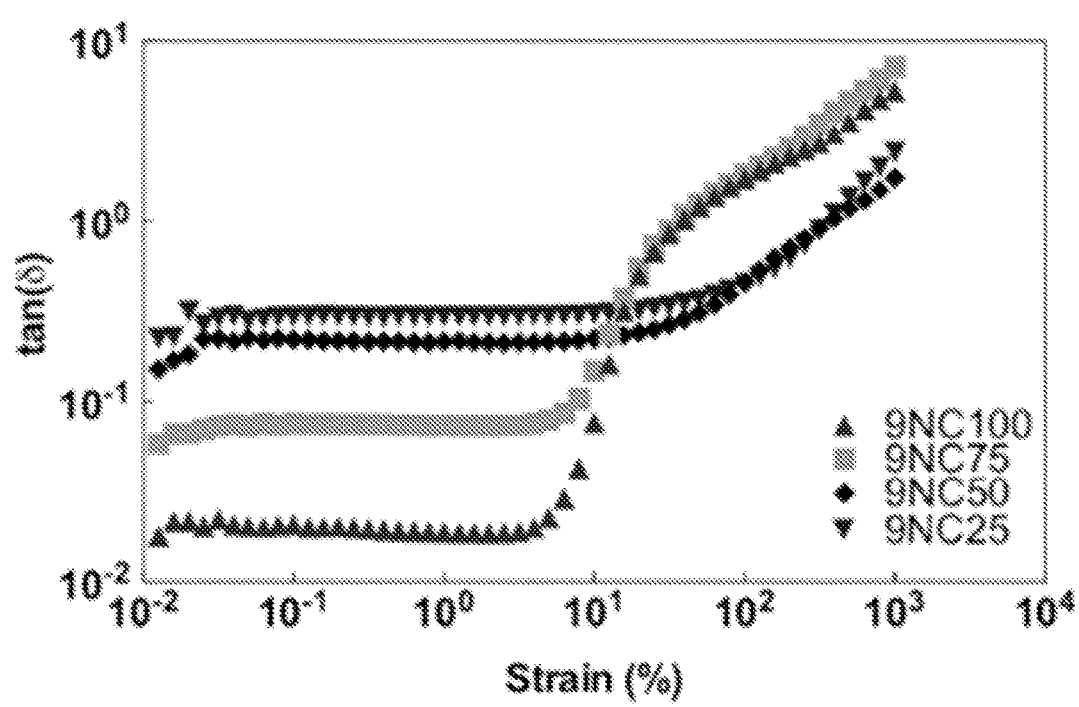
FIG. 5 shows strain sweep curves representative of compositions 9NC100, 9NC75, 9NC50, and 9NC25.
Figure 7:
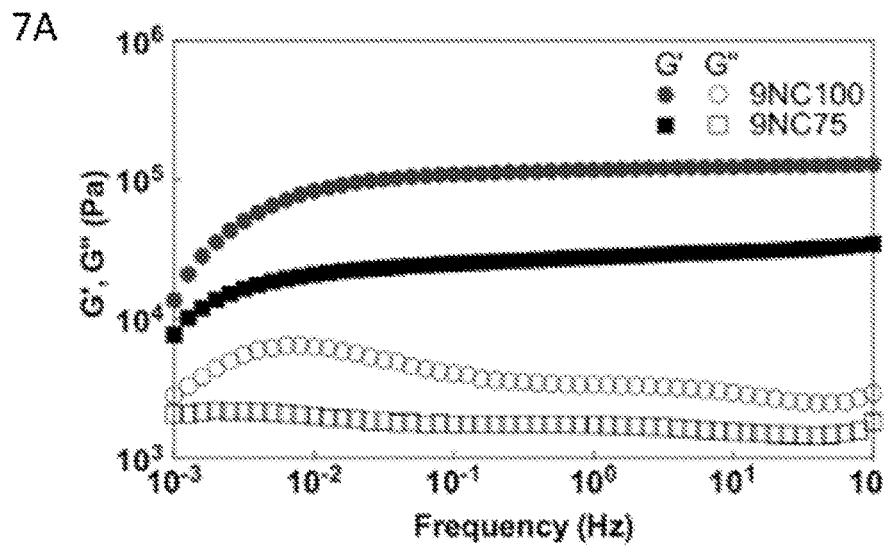
FIG. 7A shows frequency sweep curves representative of compositions 9NC75 and 9NC100 at 37° C.
FIG. 7B shows frequency sweep curves representative of compositions 9NC25 9NC50 at 37° C.
Figure 7:
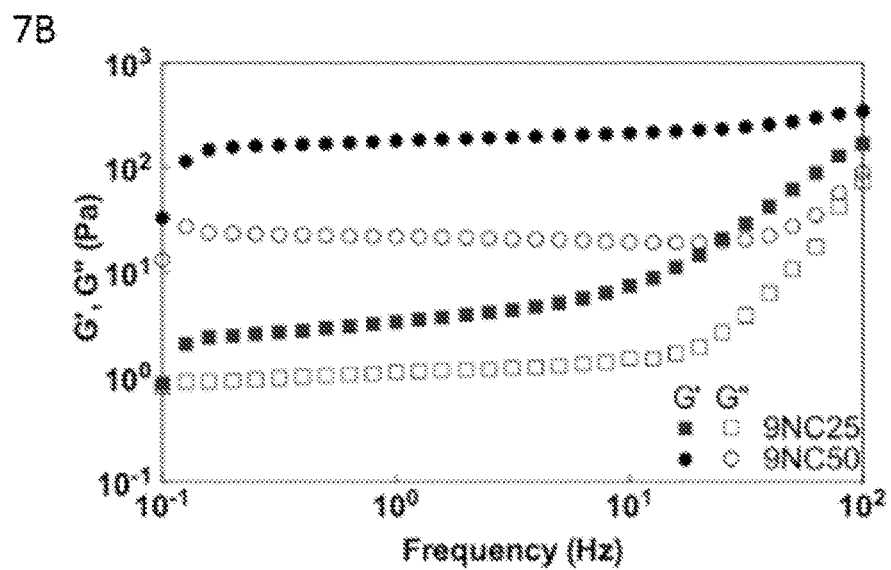
Figure 8:
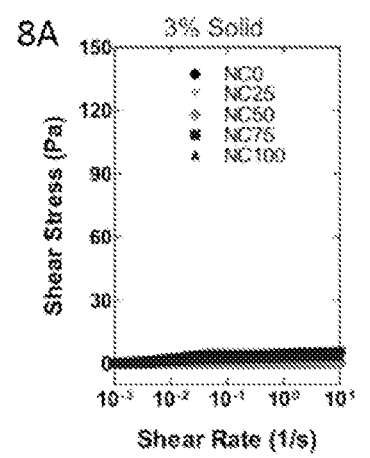
FIG. 8A shows yield stress curves representative of compositions comprising 3 total weight percent solids.
FIG. 8B shows yield stress curves representative of compositions comprising 6 total weight percent solids.
FIG. 8C shows yield stress curves representative of compositions comprising 9 total weight percent solids.
Figure 8:
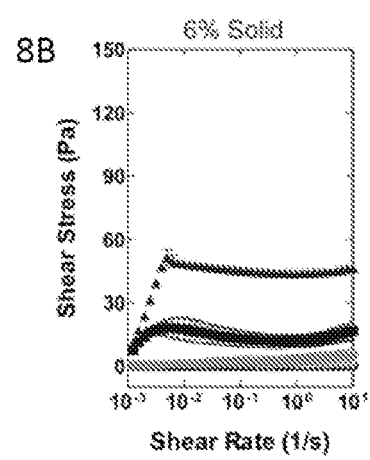
Figure 8:
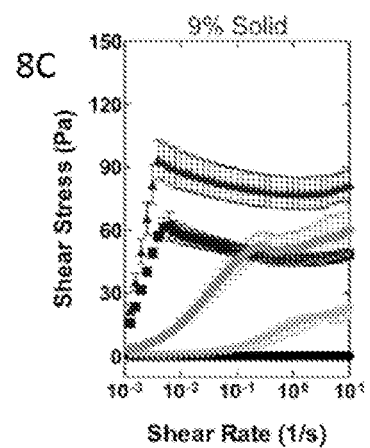
Figure 9:
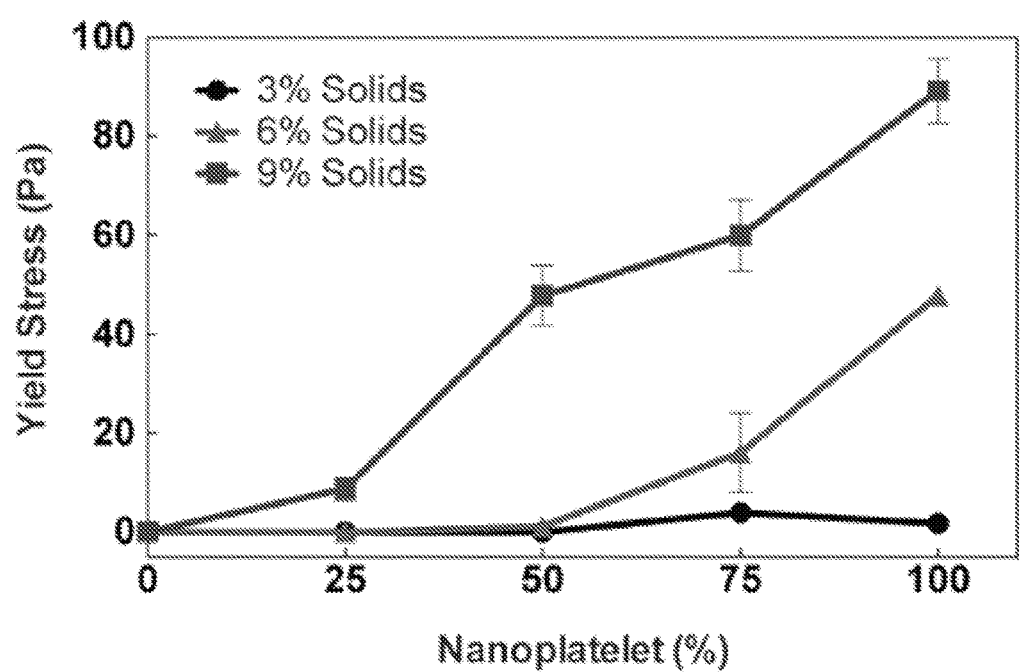
FIG. 9 shows the yield strength of compositions comprising 3, 6, and 9 total weight percent solids as a function of increasing concentrations of silicate nanoplatelets.

Silicate addition to gelatin modulated the rheological response of the compositions, resulting in a shear thinning behavior observed at 37° C. Preliminary investigations using a 22-gauge needle indicated that all silicate-containing compositions could be injected and form self-supporting structures, suggesting the presence of a yield stress and recovery potential. Linear oscillatory shear rheology showed that the crossover frequency was below 0.001 Hz for 9NC75 and 9NC100, maintaining solid-like (G'>G") properties over the tested frequency range. Strain sweeps were performed at 1 Hz and indicated a crossover point when $\tan(\delta)=1$ that decreased with increasing silicate loading, as shown in FIG. 5. Frequency sweeps were performed at 37° C. Compositions 9NC25, 9NC50, 9NC75, and 9NC100 exhibited increased moduli for compositions with higher nanoplatelet loading, as shown in FIG. 7. Oscillatory strain into the non-linear regime illustrated yielding behavior, an important parameter for designing hydrogels for minimally invasive therapies. Yield stress of gels as a function of nanoplatelet loading and total solid weight percent (3%, 6% and 9% solid) is shown in FIG. 8. In oscillatory shear rate sweeps, the yield stress was defined as a 5% departure of the stress from the initial linearity on a stress-strain plot. Tests were performed at 37° C., where gelatin readily flows and lacks a yield stress. An increase in the silicate concentrations from 0% (9NC0) to 100% (9NC100) increased the yield stress from 2 Pa to 89 Pa, as shown in FIG. 9. A yield stress was observed in 9NC100 but not in 9NC0, suggesting that the yield stress behavior was derived from the presence of the dispersed nanoplatelets in the hydrogel composition, consistent with the known shear thinning capability of nanoplatelets. Because increasing the concentration of gelatin reduces the yield stress, the presence of higher concentrations of gelatin eased delivery of the composition by injection.

Example 7. Gel Recovery and Aging

Figure 10:
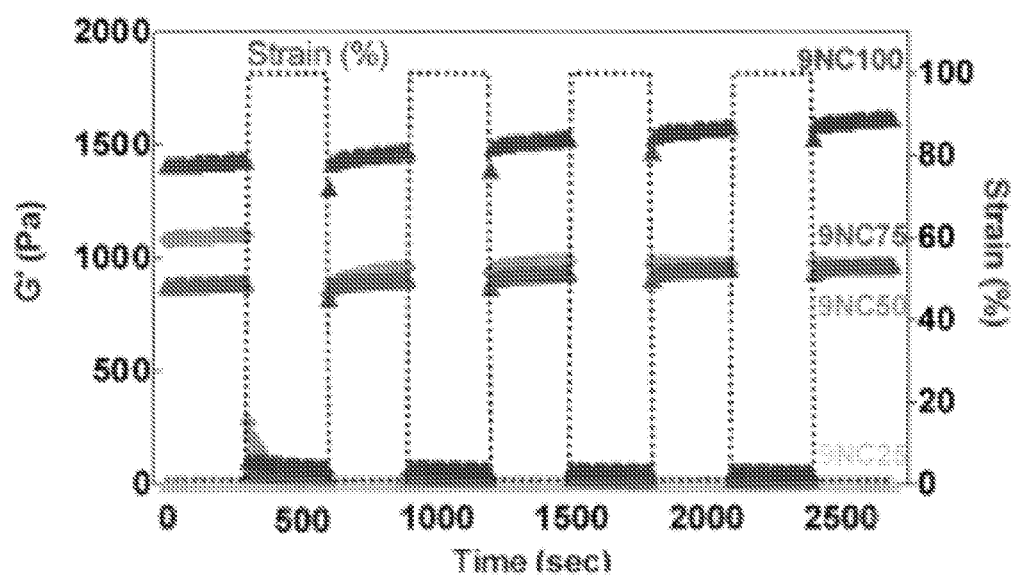
FIG. 10 shows oscillatory strain amplitude curves representative of compositions 9NC100, 9NC75, 9NC50, and 9NC25.
Figure 11:
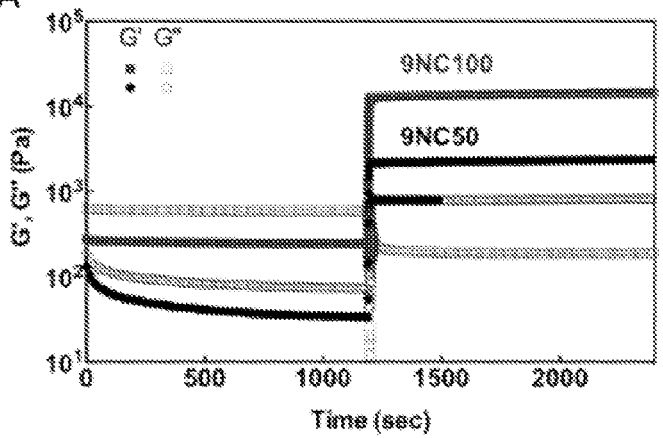
FIG. 11A illustrates recovery curves representative of compositions 9NC100 and 9NC50 from 0 seconds to 2500 seconds.
FIG. 11B illustrates recovery curves representative of compositions 9NC100 and 9NC50 from 1150 seconds to 1220 seconds.
FIG. 11C illustrates aging curves representative of composition 9NC100 from 0 seconds to 50000 seconds.
Figure 11:
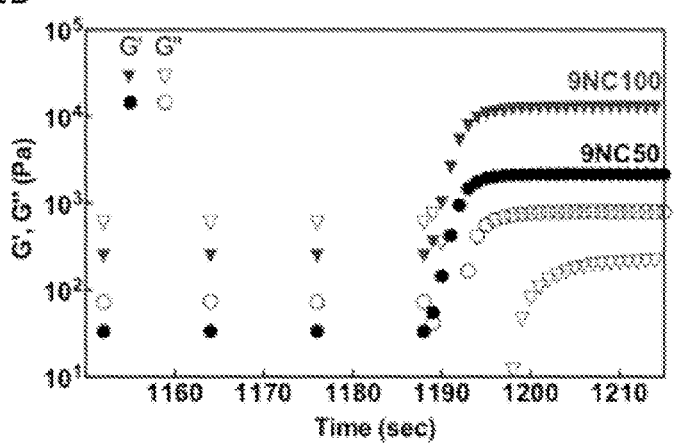
Figure 11:
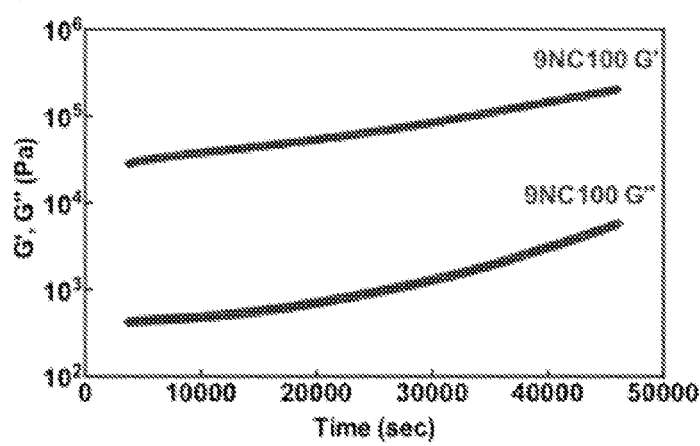

Recovery of the elastic gel strength in less than 10 seconds was observed in compositions for nanoplatelet loadings greater than 50% (9NC50, 9NC75, and 9NC100). Recovery was tested by straining above the crossover point, observed from strain sweeps, to break the network, resulting in G">G', followed by removal of the strain. Such rapid self-healing after the removal of stress can prevent material flow after application to a wound site. This provides a significant advantage over self-assembling peptides, which risk being washed away because they have relatively long self-healing times after the deformation of physically crosslinked networks. FIG. 10 shows four cycles of high (100%) to low (1%) oscillatory strain amplitudes and the resulting composition moduli. These results indicate rapid recovery of the storage modulus after repeated application of high oscillatory strain amplitudes, suggesting rapid recovery of the physically crosslinked networks. After four cycles of high and low oscillatory strain, the modulus observed for composition 9NC50 during large amplitude strain oscillations was 80% lower than the initial modulus. At higher silicate loading (9NC75 and 9NC100), the moduli were 33% and 29% lower compared to the initial values. Extended monitoring indicated that after 30 seconds the moduli reached asymptotic values, indicating completion of the healing process, as shown in FIG. 11. Aging of composition 9NC100 was observed when samples were monitored over a period of hours at 1% strain, 1 Hz, and is shown in FIG. 11c. The effects of aging were able to be countered by application of high shear rates ($10 \text{ s}^{-1}$) prior to testing, which returned moduli to their initial, non-aged values.

Example 8. Zeta Potential Measurements

Figure 12:
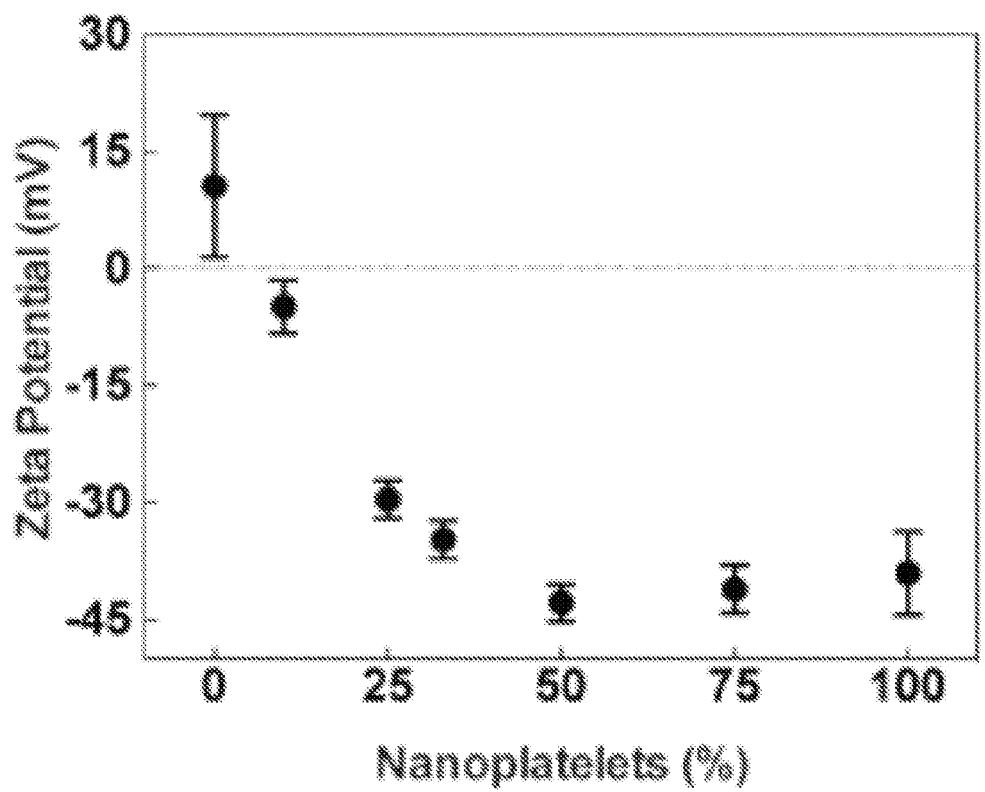
FIG. 12 shows zeta potential curves for solutions comprising 0 weight percent to 100 weight percent silicate nanoplatelets.

Solutions of silicate nanoplatelets possessed a zeta potential of −39 mV, whereas gelatin solutions had a zeta potential of 10 mV and are shown in FIG. 12. Because the two components had opposite charges, electrostatic interactions between silicate and gelatin were expected. This was also supported by earlier findings which showed that strong interactions between montmorillonite (another type of silicate clay) and gelatin can function to increase the sol-gel transition temperature of the composite. Zeta potential measurements suggest that electrostatic interactions between nanoplatelets and gelatin contributed to the observed increase in the thermal stability.

Example 9. In Vitro Blood Clotting Studies

Mouse monocyte/macrophage RAW 264.7 cells were procured from the ATCC. RAW 264.7 cells were grown in DMEM medium supplemented with 10% FBS and 1% penicillin/streptomycin at 37° C. in 5% $CO_2$. Lipopolysaccharide (LPS) was obtained from InvivoGen. RAW 264.7 macrophages were suspended in different composition of gelatin and silicate at a concentration of $3 \times 10^6$ cells/mL and plated at a density of 2,000 cells/well and grown for 24 h. As controls, RAW cells were untreated or treated with 100 ng/mL of LPS. An ELISA assay (SA Biosciences) was performed according to the manufacturer's protocol on the supernatants of different groups to quantify the secreted cytokines IL-6 and TNF-α by the RAW cells.

The cell viability of RAW cells in the presence of gelatin and silicate for 24 h was measured with Cell Titer 96 Aqueous Non-Radioactive Cell Proliferation MTS Assay (Promega) according to manufacturer's protocol using plate reader at 490 nm absorbance. In order to eliminate possible absorbance from silicate or gelatin components, the absorbance values with gelatin, silicate, and hydrogel compositions, without cells, was measured. These absorbance values were subtracted from the corresponding absorbance values for gelatin, silicate, and hydrogel compositions, with cells. This resulted in reading the absorbance values of only viable cells. Each tested hydrogel was measured in three separate wells.

A clotting time assay was performed using the following general procedure: A solution of citrated blood was prepared and 10% (v/v) 0.1 M calcium chloride ($CaCl_2$) was then added, followed by vortexing for 10 seconds. 50 µL of the blood/$CaCl_2$ mixture was then deposited into sequential wells on a 96 well plate. At selected time points, each well was washed with 9 g/L saline solution to halt clotting. The liquid was immediately aspirated and washes repeated until the solution was clear, indicating removal of all soluble blood components. Compositions were injected via syringe into the base of the well plates prior to adding blood. Final clotting time was marked in the well that formed a uniform clot, with no change in clot size in subsequent wells.

For quantification and imaging of interfacial interactions, anticoagulated whole blood was centrifuged for 2 minutes to separate red blood cell-rich (RBC-rich) and RBC-poor phases at 6,000 rpm. A liquid solution of fluorescently labeled nanoplatelet was mixed with the RBC-rich and poor blood phases. Dilute solutions of RBC-rich/nanoplatelet and RBC-poor/nanoplatelet were mixed and deposited onto glass slides for fluorescent imaging.

i. Toxicity and Cell Viability

Figure 13:
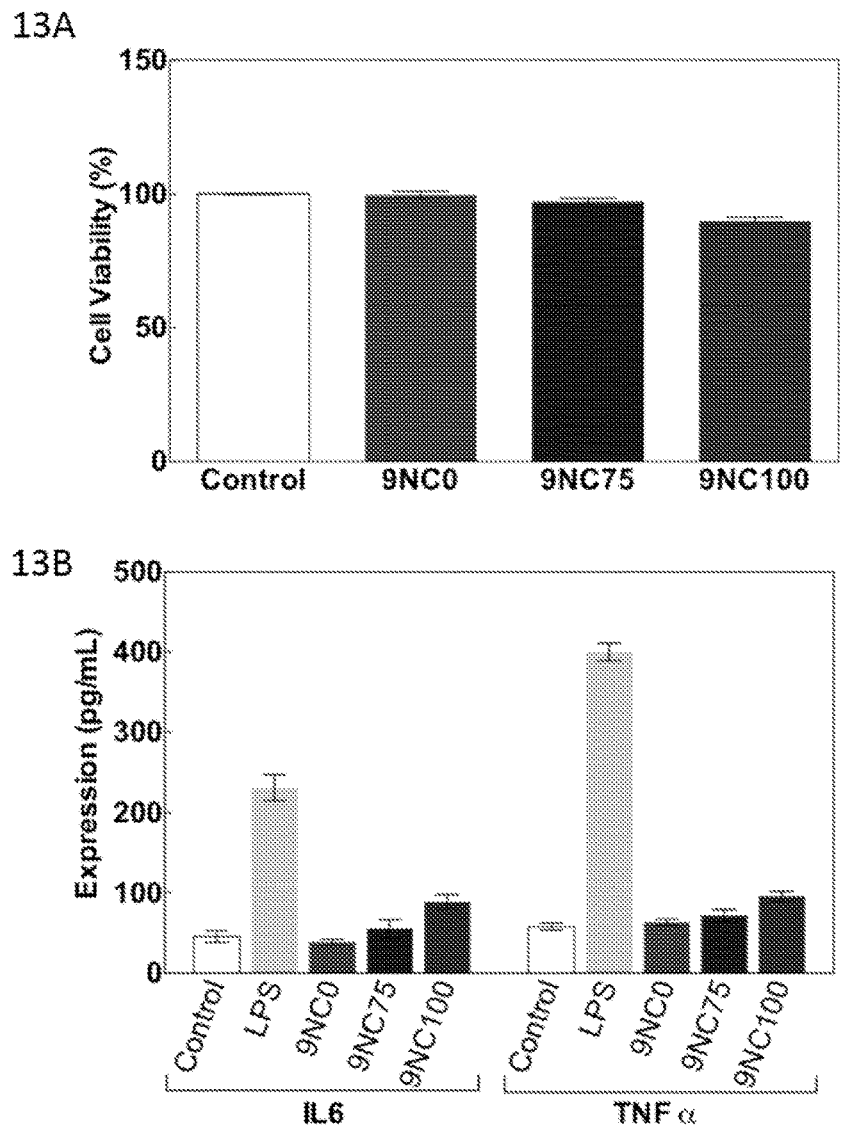
FIG. 13A shows toxicity profiles representative of compositions 9NC0, 9NC75, and 9NC100 as determined by MTS assay with RAW macrophages.
FIG. 13B shows toxicity profiles representative of compositions 9NC0, 9NC75, and 9NC100, as determined by secretion of pro-inflammatory cytokines, IL-6 and TNF-α, from RAW 264.7 macrophages after 24 h exposure.

Preliminary in vitro studies indicate that the compositions induced minimal cytotoxic effect or inflammatory response with gelatin-silicate nanoplatelet compositions having higher cell viability and lower inflammatory response than NC100 gels. Toxicity profiles of compositions 9NC0, 9NC100, and 9NC75 with RAW macrophages as determined by a) MTS assay and b) secretion of pro-inflammatory cytokines, IL-6 and TNF-α, from RAW 264.7 macrophages after 24 h of exposure are shown in FIG. 13.

ii. In Vitro Hemostatic Evaluation

Figure 14:
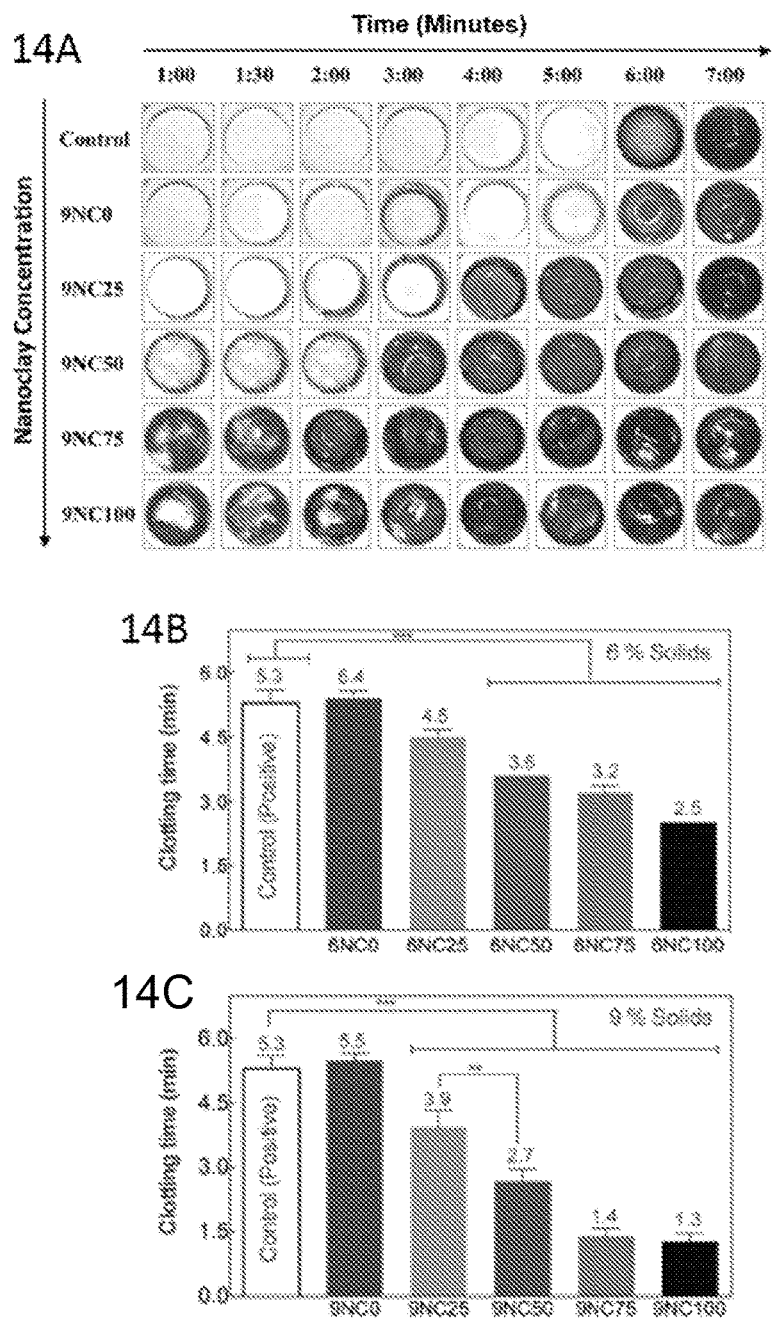
FIG. 14A shows whole blood clotting in the presence of compositions 9NC0, 9NC25, 9NC50, 9NC75, and 9NC100 in control wells compared to a control (blood in uncoated wells).
FIG. 14B illustrates whole blood clotting time in the presence of compositions 6NC0, 6NC25, 6NC50, 6NC75, and 6NC100 compared to a control (blood in uncoated wells).
FIG. 14C illustrates whole blood clotting time in the presence of compositions 9NC0, 9NC25, 9NC50, 9NC75, and 9NC100 compared to a control (blood in uncoated wells).

The incorporation of silicate nanoplatelets into gelatin led to a decrease in the observed clotting time in vitro. The hemostatic ability of the compositions was evaluated by monitoring the clotting time of whole blood in contact with the composition surfaces in 96-well plates. Under normal conditions, human blood coagulates in about 5 to about 6 minutes. Similar clotting times (5.2±0.5 minutes) for whole blood were observed in control wells containing neither gelatin nor a composition. A slight color change was observed for wells in contact with gelatin after about 5 minutes. This color change was attributed to the tamponade ability of gelatin (i.e., absorption of blood by gelatin). Gelatin is hygroscopic and could absorb the fluid components of whole blood but did not stimulate clot formation within 5 minutes. The addition of nanoplatelets to gelatin reduced blood clotting time in a dose-dependent manner. As demonstrated in FIG. 14 the clotting time was decreased for higher nanoplatelet concentrations. Compositions 9NC25, 9NC50, and 9NC75 reduced the clotting time by 32%, 54%, and 77%, respectively when compared to the control (blood in uncoated wells). The representative images of wells at select time points, shown in FIG. 14, clearly highlight the earlier formation of a clot in compositions with higher nanoplatelet loadings. This was attributed to the strong negative charge of the synthetic silicate nanoplatelets that can facilitate concentration of clotting factors near the composition surface.

iii. Rheological Measurements

Figure 15:
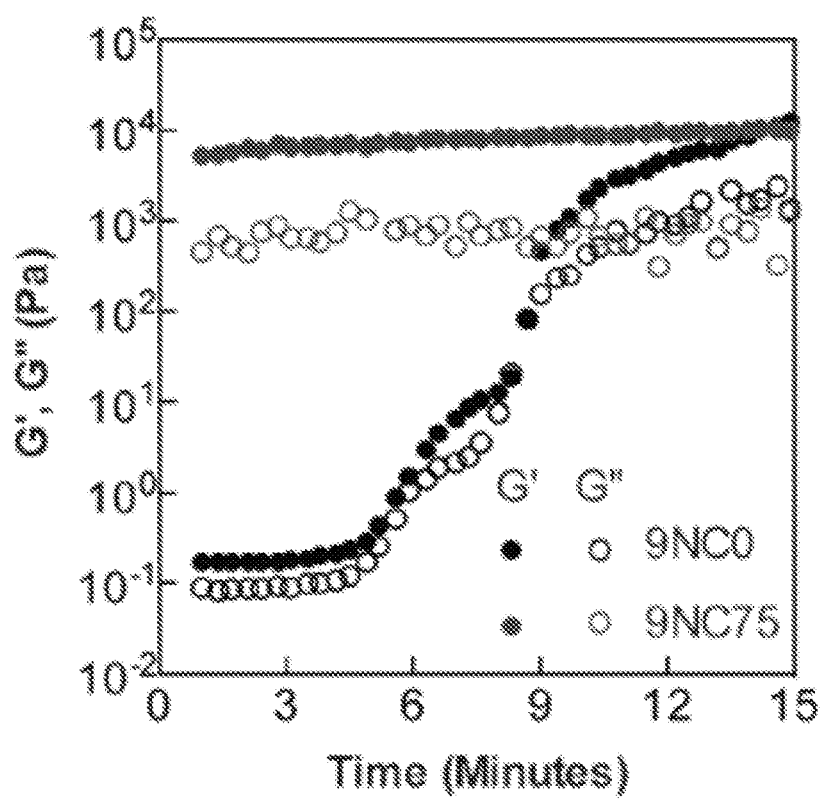
FIG. 15 shows small amplitude oscillatory time sweeps representative of blood in contact with 9NC0 and 9NC75.
Figure 16:
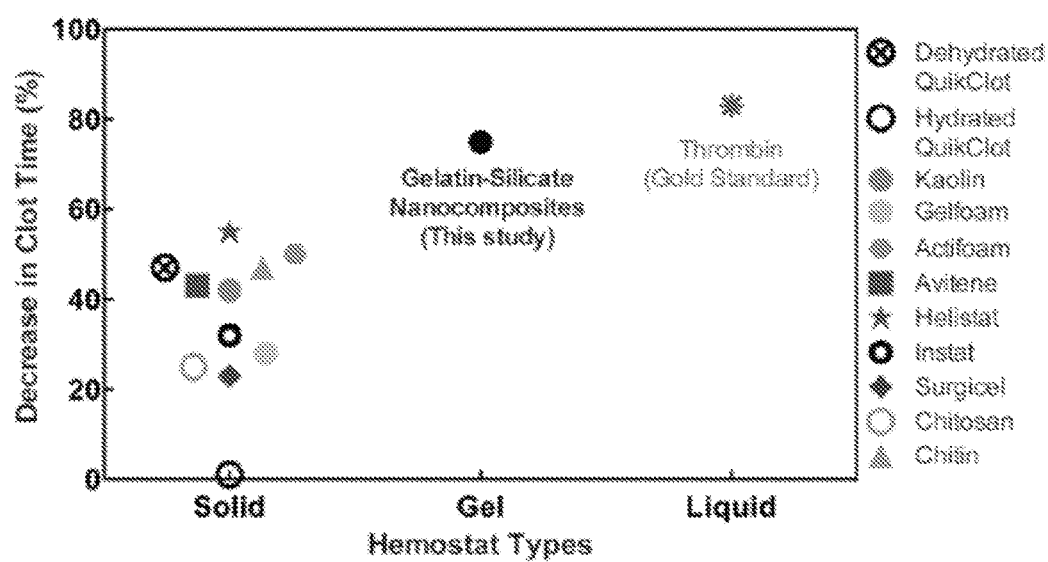
FIG. 16 shows the observed clotting time of blood in contact with gelatin-silicate nanoplatelet compositions as provided herein compared to the observed clotting time of blood in contact with other hemostatic products.

Decreased clotting times of blood in contact with the compositions were also observed through rheological measurements. Small amplitude oscillatory time sweeps of blood in contact with gelatin or gelatin-silicate compositions were performed to evaluate clotting kinetics and are shown FIG. 15. Clotting induced an increase in the elastic modulus of the gelatin-clot system from $10^{-1}$ to $10^4$ Pa. Whole blood in contact with gelatin clotted in 5-7 minutes, which corresponds to previously reported data. When gelatin was replaced with a silicate-gelatin composition, the clotting transition occurred prior to the initiation of measurements, reflecting a large reduction in the clotting time. Comparing the decrease in clotting time observed with compositions to other reported hemostatic products, the improvement exceeds many solid hemostats and was similar to recorded values for thrombin-based hemostats, as shown in FIG. 16.

iv. Thrombus Weight

Figure 17:
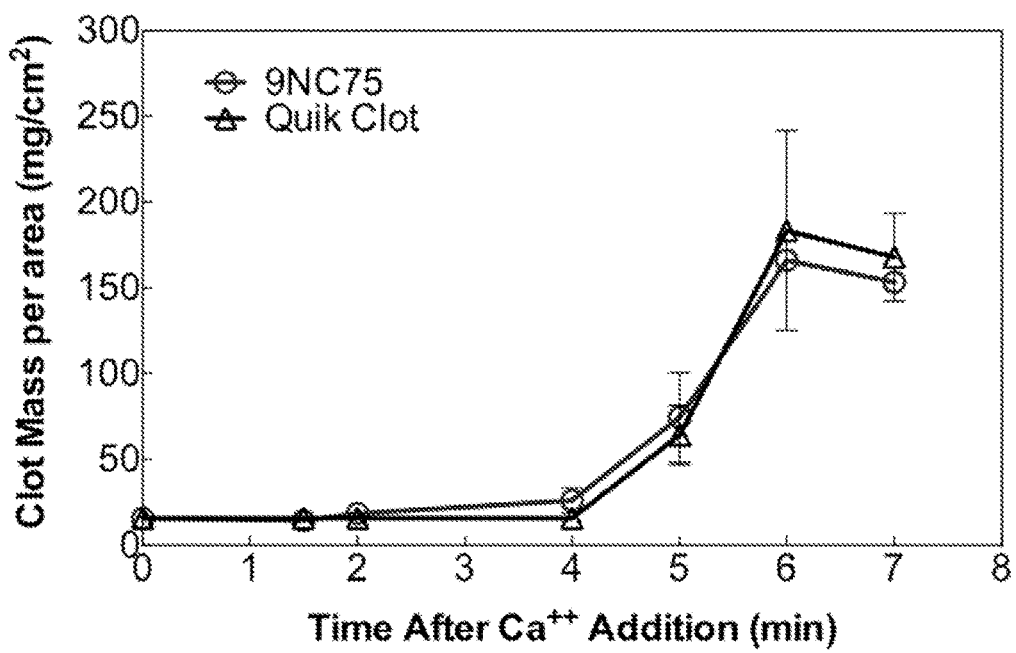
FIG. 17 shows a time series curve representative of blood clot formation for composition 9NC75 and QuikClot™.

Gelatin-silicate compositions and powdered QuikClot™ samples were weighed into 2 mL Eppendorf tubes. Compositions were centrifuged to standardize the surface area exposed. Citrated blood was reactivated by 10% (v/v) 0.1 m $CaCl_2$. 100 µL of solution (10 µL $CaCl_2$ and 90 µL whole blood) was added to each Eppendorf tube. At each measured time point, clotting was stopped by addition of 200 µL sodium citrate solution (0.109 m). Any liquid was removed from the Eppendorf, leaving only clotted blood. The Eppendorf tubes were reweighed to determine the mass of clot produced in the tube. Clot mass was normalized to the area exposed to the composition. The same area was used for the commercial hemostat sample. Time series of thrombus weight per area for composition 9NC75 and hydrated QuikClot™ powder are shown in FIG. 17, and reflect similar trends in the formation of a clot. The composition, an injectable system, begins to form a measurable clot at 2 minutes while QuikClot™, a solid hemostat, begins clotting after 4 minutes. Subsequent time points are not statistically different from one another, indicating that the ability of 9NC75 to form a clot is comparable to that of the commercial QuikClot™ powder. The background mass per area of 15 mg/$cm^2$ corresponds to residual liquid remaining after the washing step is performed to halt clotting.

v. Blood Clot Strength

Figure 6:
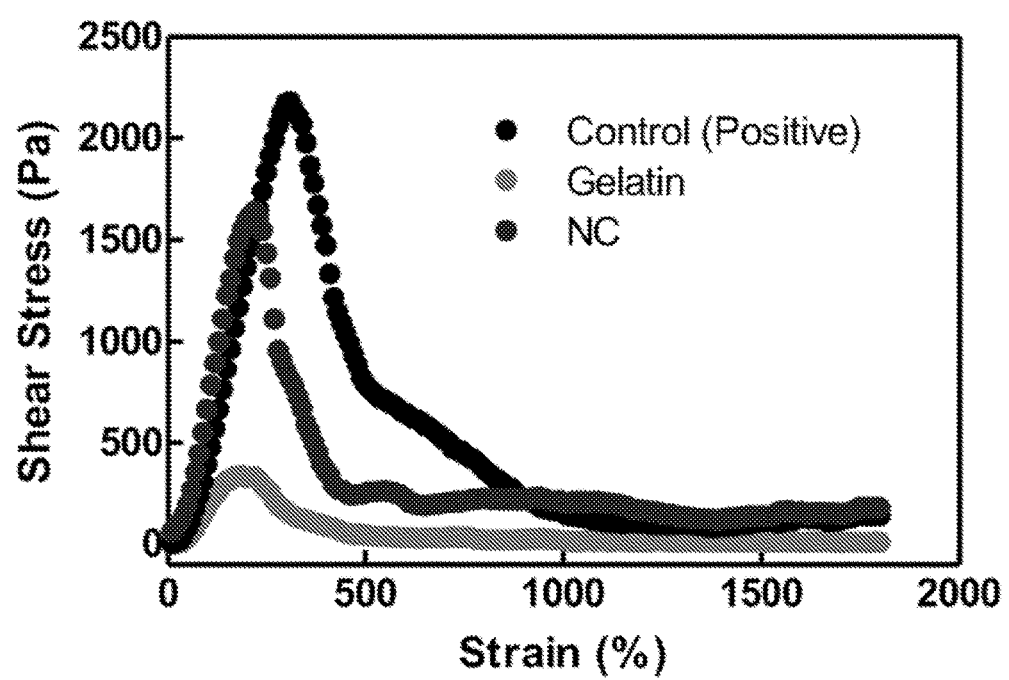
FIG. 6 compares the effects of gelatin and composition 9NC75 on blood clot strength.

Blood clot strength was preserved in gelatin-silicate composition-blood systems. Clot strength, characterized by the peak shear stress attained in a linearly increasing strain experiment, is a parameter important for establishing hemostasis. More rigid clots are more likely to embolize while more pliable clots are ineffective. Rotational strain sweep of clot and clot-composition systems show a decreased peak stress for clots in contact with gelatin compared to the peak stress of a clot alone. However, the peak stress for a 9NC75-clot system has a comparable peak stress to that of the clot alone. The results indicate that the clot could sustain a peak shear stress of 2.4±0.3 kPa, while the gelatin-clot system had a peak shear stress of 0.5 kPa. The liquid-like properties of gelatin (G''>G') at 37° C. compromise the mechanical stability of the system. Compositions tested under the same conditions reached a maximum shear stress of 1.0±0.09 kPa. In the presence of gelatin-silicate composition, the shear stress of a composition-clot was 1.9±0.6 kPa, which is comparable to the peak stress borne by the clot, as shown in FIG. 6.

vi. Platelet Aggregation

It was hypothesized that the surface charge of the compositions facilitated platelet aggregation or activation of clotting factors that ultimately enhanced the hemostatic activity. To confirm this, a channel was generated within a gelatin-silicate composition and subsequently filled with blood. It was observed that platelets aggregated near the composition surface, which was not observed in control experiments on gelatin or plastic surfaces. This indicates that composition surfaces might be effective in attracting blood components.

Figure 18:
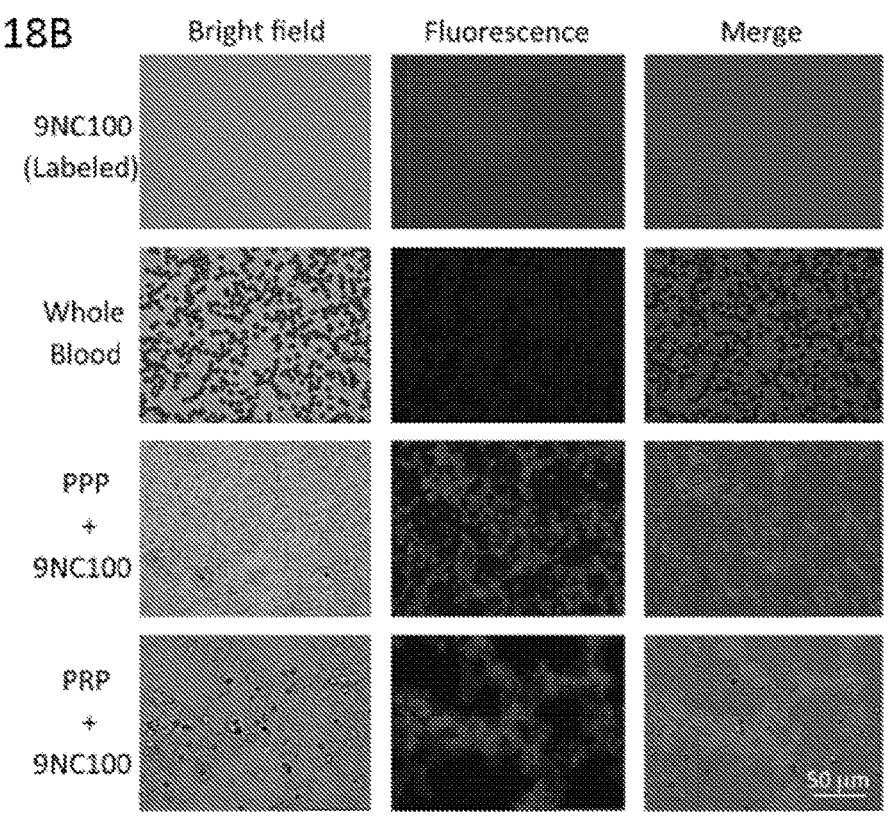
FIG. 18A shows fluorescent images representative of composition 9NC100 in contact with a clot.
FIG. 18B shows fluorescent images representative of composition 9NC100, whole blood, 9NC100+platelet poor plasma (PPP), and 9NC100+platelet rich plasma (PRP).

Observations in the presence of platelet rich plasma (PRP) and platelet poor plasma (PPP) indicated that components in both plasma types were co-localized with silicates, forming aggregates around the silicates. This co-localization and protein adsorption to the composition surfaces could be driven by electrostatic or hydrophobic interactions, which have been shown to determine protein adsorption to biomaterial surfaces. As shown in FIG. 18B, the top row of images shows a uniform fluorescence from a silicate nanoplatelet solution. The second row (whole blood) shows blood cells with a minimal fluorescent signature. The mixture of labelled 9NC100 and PPP showed co-localization of the plasma components with the silicate nanoplatelets (third row). The same was observed for the nanoplatelets and PRP (fourth row). The uniform fluorescence of the nanoplatelets is disrupted by the presence of blood components, suggesting a change in the interactions between nanoplatelets. The co-localization of silicates and blood components is thought to originate from plasma proteins and blood cells interacting with the charged surfaces of silicate nanoplatelets, increasing blood component concentrations surrounding the composition. Previous studies have shown that charge interactions can initiate the coagulation cascade, such as the interactions of GPIb-V receptors (negative) with platelets and von Willebrand factor (positive) with collagen.

Example 10. In Vivo Biocompatibility of Gelatin-Silicate Compositions

Male Wistar rats (n=20; 200-250 g) were obtained from Charles River (Wilmington, Mass., USA), housed in the local animal care facility (PRB, Cambridge, Mass., USA). Anesthesia and analgesia were achieved by isoflurane inhalation (2.0-2.5%) and subcutaneous carprofen administration (5 mg/kg/d). All experiments were conducted according to the NIH "Guide for the Care and Use of Laboratory Animals", and approved by the local animal care committee (HMA Standing Committee on Animals; protocol number 05055).

Dorsal skin incisions (1 cm in length) were conducted and a small subcutaneous pocket was generated by blunt preparation. Gelatin-silicate compositions (n=8; 200 µl) were injected or QuikClot™ samples (n=8; 200 µl) were implanted, respectively. The wounds were anatomically closed. After 3 and 28 days, the animals were euthanized by $CO_2$ inhalation, and the implants as well as adjacent tissue were explanted and further processed for histological analyses.

Median laparotomies were performed and the central liver lobe was exposed (n=12 rats). After draping the surrounding situs with filter paper for blood collection, a standardized circular liver laceration was created by gluing a plastic disc (d=10 mm) to the surface and superficially excising this area with a blade Immediately after injury, a gelatin-silicate composition (n=5; 200 µl) or QuikClot™ (n=2; 200 µl) was applied on the site of lesion. Five minutes after the bleeding had been stopped, the abdomen was anatomically closed, and the animals were allowed to recover from anesthesia. After 28 days, the animals were euthanized by $CO_2$ inhalation, and the site of injury was inspected. In order to examine the principal lethality of the liver bleeding model, control rats (n=5) underwent liver injury without subsequent application of a hemostat. In all liver bleeding experiments, the amount of bleeding was determined by weighing filter papers used to collect lost blood after removal.

Histological analyses were conducted as previously published (see Assmann, et al., *Biomaterials*, 2013, 34(25): 6015-6026). In brief, paraformaldehyde-fixed cryo-sections (6 µm) of all explants were stained with hematoxylin/eosin and microscopically analyzed.

i. Dorsal Subcutaneous Injection

Figure 19:
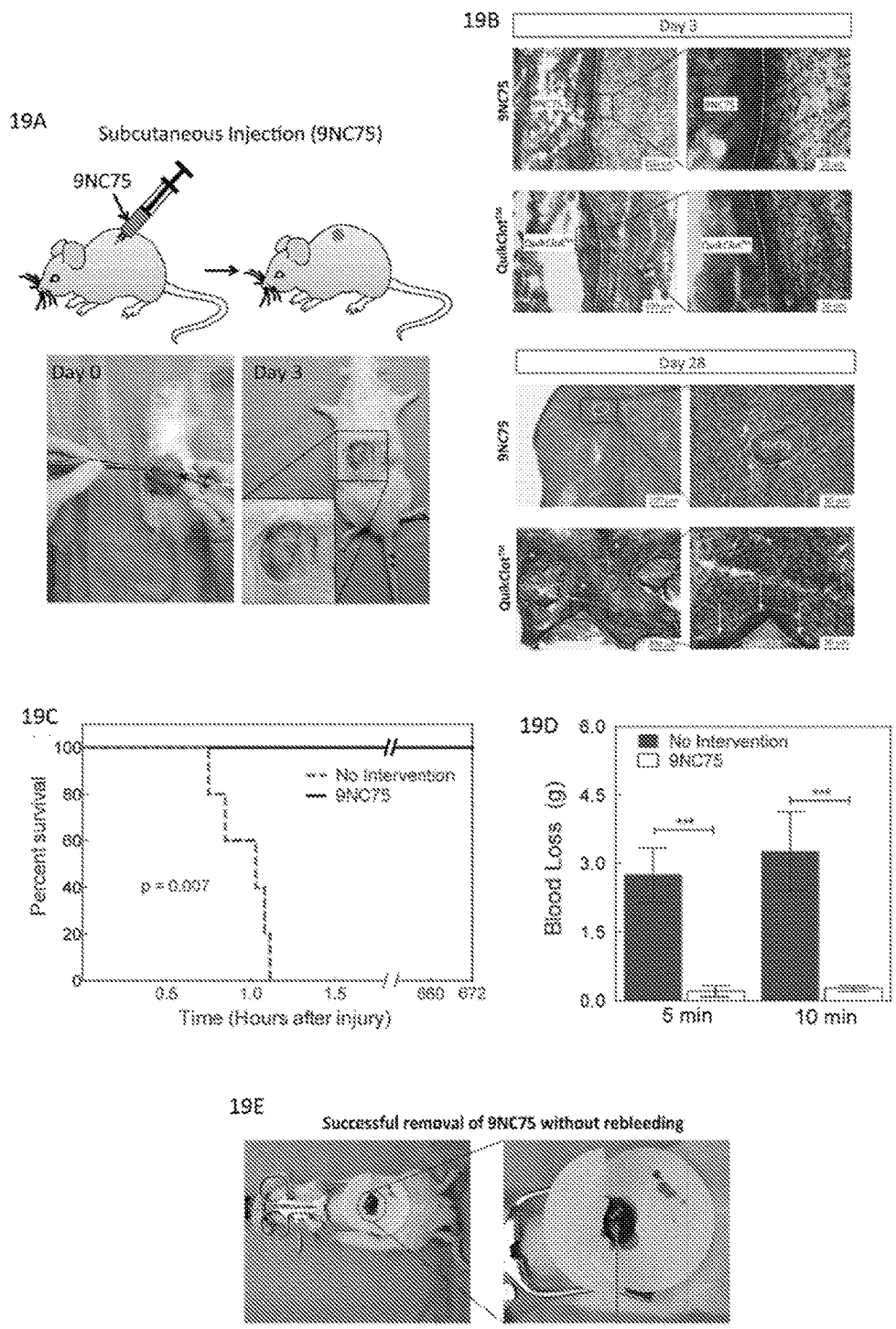
FIG. 19A illustrates dorsal subcutaneous injections in rats via 1 cm incisions using composition 9NC75 and Quik-Clot™.
FIG. 19B shows images representative of composition 9NC75 and QuikClot™ after 3 days and 28 days post-dorsal subcutaneous injections.
FIG. 19C illustrates the survival rate of rats treated with composition 9NC75 compared to untreated rats.
FIG. 19D illustrates the blood loss of rats treated with 9NC75 compared to untreated rats after 5 minutes and 10 minutes.
FIG. 19E shows the successful removal of composition 9NC75 from a treated rat without rebleeding.

All animals survived the follow-up period of 28 days without any signs of physical impairment or systemic inflammation, and exhibited regular somatic growth. After 3 days, the implanted hemostats (9NC75 and QuikClot™) could be easily detected in the subcutaneous pockets. At day 28, the QuikClot™ particles appeared macroscopically unchanged and 9NC75 was integrated in the surrounding tissue. Hematoxylin & Eosin (H&E) staining confirmed these observations indicating that 9NC75 was predominantly degraded within 28 days after injection, while QuikClot™ did not undergo degradation. Both compositions induced an acute, locally restricted inflammatory reaction in the host, including cellular infiltration, which progressed into chronic inflammation of the surrounding tissue. The inflammatory response against QuikClot™ was substantially stronger compared to composition 9NC75, resulting in a higher density and larger area of predominantly mononuclear cellular infiltrates. Moreover, in the QuikClot™ group, dense fibrous tissue formation was detected around the implants at day 28, indicating fibrous capsule formation. Results of the dorsal subcutaneous injection studies are shown in FIG. 19.

ii. Lethal Living Bleeding

Figure 20:
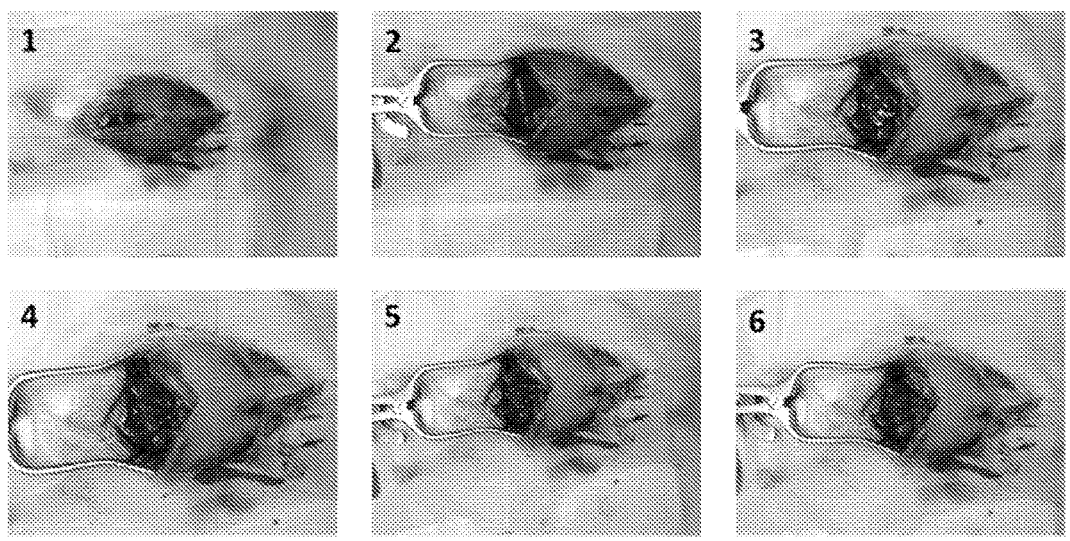
FIG. 20 shows representative images of a standardized liver bleeding model.

The principal lethality of this bleeding model was assessed in control animals (n=5) without application of a hemostat. Composition 9NC75 (n=5) and QuikClot™ (n=2) were effective in stopping relevant hemorrhage within seconds and prevented hypovolemic conditions. A log rank analysis of the early post-interventional survival data revealed significant improvement by the composition (log rank (Mantel-Cox) test: p=0.007 versus control; hazard ratio 11.5 with 95% CI 1.93-68.9). The total blood loss after 5 and 10 minutes was significantly decreased by the application of composition 9NC75 (p<0.001 versus control). The small amount of applied composition (200 µl) was more than sufficient, since the superficial parts of the composition were not soaked with blood, and thorough removal of this excess material did not cause re-bleeding. All hemostat-treated liver bleeding animals survived the complete follow-up period of 28 days without secondary hemorrhage. At explanation, no remnants of composition 9NC75 were observed and the liver presented an intact surface, whereas QuikClot™ was still present, accompanied by soft tissue adhesion to the site of lesion. These results show that the gelatin-silicate compositions offer a strong hemostatic potential for in vivo applications and is suitable to stop lethal bleeding. Representative images of the living bleeding study are shown in FIG. 20.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical composition, consisting of a gelatin derivative, silicate nanoparticles, and deionized water, wherein the composition is a homogenous hydrogel composition.

2. The composition of claim 1, wherein the ratio of silicate nanoparticles to gelatin derivative, is from about 1.0 to about 0.1.

3. The composition of claim 1, wherein the gelatin derivative is methacrylated gelatin (GelMA), acrylated gelatin, or thiolated gelatin.

4. The composition of claim 1, wherein the silicate nanoparticles comprise silicate nanoplatelets.

5. The composition of claim 4, wherein the silicate nanoplatelets comprise a positively charged edge and a negatively charged surface.

6. The composition of claim 1, wherein the overall charge of the silicate nanoparticles is negative.

7. The composition of claim 1, wherein the silicate nanoparticles are from about 5 nm to about 60 nm in diameter.

8. The composition of claim 1, wherein the silicate nanoparticles are from about 0.5 nm to about 2 nm in thickness.

9. The composition of claim 1, wherein the composition has a yield stress of from about 1 Pa to about 200 Pa.

10. The composition of claim 1, wherein the composition flows upon application of a pressure greater than the yield stress.

11. A homogenous hydrogel composition consisting of a gelatin derivative, silicate nanoparticles, and deionized water, wherein the composition is prepared according to a process comprising:
(a) combining the silicate nanoparticles and deionized water to form a first mixture; and
(b) adding the gelatin derivative thereof to the first mixture to form the homogenous hydrogel composition.

12. The composition of claim 1, wherein the gelatin derivative is methacrylated gelatin (GelMA).

13. The composition of claim 1, wherein the gelatin derivative is acrylated gelatin.

14. The composition of claim 1, wherein the gelatin derivative is thiolated gelatin.

15. A method of treating a wound, comprising administering to a patient in need thereof, a composition of claim 1.

16. The method of claim 15, wherein the wound comprises a wound of the skin on the patient.

17. The method of claim 15, wherein the wound comprises a wound of an organ in the patient.

18. The method of claim 15, wherein the wound comprises a wound of a blood vessel in the patient.

19. The method of claim 15, wherein the composition is administered by injection or topical administration.

20. The method of claim 15, wherein prior to administration, the composition is preloaded into a sterile syringe, preloaded onto a surface of a sterile bandage, preloaded onto a surface of a sterile surgical staple, preloaded onto a surface of a sterile surgical suture, or preloaded onto a sterile surgical sponge.

21. The method of claim 15, wherein treating a wound comprises reducing the blood clotting time compared to the blood clotting time of an untreated wound.

22. The method of claim 21, wherein the blood clotting time is reduced by about 25% to about 85% compared to the blood clotting time of an untreated wound.

23. A process of preparing the composition of claim 1, comprising:
(a) combining the silicate nanoparticles and deionized water to form a first mixture; and
(b) adding the gelatin derivative to the first mixture to form said composition.

\* \* \* \* \*

UNITED STATES PATENT AND TRADEMARK OFFICE
CERTIFICATE OF CORRECTION

PATENT NO. : 10,034,958 B2  
APPLICATION NO. : 14/899727  
DATED : July 31, 2018  
INVENTOR(S) : Akhilesh K. Gaharwar et al.

Page 1 of 1

It is certified that error appears in the above-identified patent and that said Letters Patent is hereby corrected as shown below:

In the Specification

In Column 1, after Line 11 (approx.), insert:  
-- FEDERALLY SPONSORED RESEARCH OR DEVELOPMENT  
This invention was made with government support under Contract Nos. W911NF-13-D-0001 and W911NF-07-D-0004 awarded by the Department of Defense. The government has certain rights in the invention. --

Signed and Sealed this  
Eleventh Day of October, 2022

Katherine Kelly Vidal  
*Director of the United States Patent and Trademark Office*